(12) United States Patent
Day et al.

(10) Patent No.: US 7,829,301 B2
(45) Date of Patent: Nov. 9, 2010

(54) SCREENING ASSAYS FOR BINDING ANTAGONISTS OF THE AMD-ASSOCIATED VARIANT OF FACTOR H (H384)

(75) Inventors: Anthony J. Day, Manchester (GB); Simon J. Clark, Oxford (GB); Paul N. Bishop, Manchester (GB); Robert B. Sim, Oxford (GB); Anna M. Blom, Lund (SE); Dick Heinegard, Lund (SE)

(73) Assignee: The University of Manchester (GB)

( * ) Notice: Subject to any disclaimer, the term of this patent is extended or adjusted under 35 U.S.C. 154(b) by 481 days.

(21) Appl. No.: 11/837,471

(22) Filed: Aug. 10, 2007

(65) Prior Publication Data

US 2008/0171343 A1    Jul. 17, 2008

Related U.S. Application Data

(60) Provisional application No. 60/838,770, filed on Aug. 18, 2006.

(51) Int. Cl.
G01N 33/53 (2006.01)

(52) U.S. Cl. .......................... 435/7.21; 435/2; 435/7.1; 436/501; 436/518; 436/522; 422/50; 422/61; 530/300; 530/350

(58) Field of Classification Search ........................ None
See application file for complete search history.

(56) References Cited

PUBLICATIONS

Sjoberg et al. Molecular Immunology, Sep. 2007, vol. 44, No. 16, p. 3988.*
Aslam and Perkins, J. Mol. Biol. (2001) 309:1117-1138.
Blackmore et al., J. Immunol. (1996) 157:5422-5427.
Blackmore et al., J. Immunol. (1998) 160:3342-3348.
Day et al., Immunogentics (1998) 27:211-214.
Edwards et al., Science (2005) 308:421-424.
Elward et al., J. Biol. Chem. (2005) 280:36342-36354.
Gardner ot al., Biochem. Biophys. Res. Commun. (1980) 94:61-67.
Gershov et al., J. Exp. Med. (2000) 192:1353-1363.
Giannakis et al., Eur. J. Immunol. (2003) 33:962-969.
Haines et al., Science (2005) 308:419-421.
Heingard et al., J. Biol. Chem. (1986) 261:13866-13872.
Herbert et at., J. Biol. Chem. (2006) 281:16512-16520.
Jarva et al., J. immunol. (1999) 163:3957-3962.
Kardys et al., J. Am. Coil. Cardiol. (2006) 47:1568-1575.
Klein et al., Science (2005) 308:385-389.
Kliffen et al., Arch. Opthalmol. (1996) 114:1009-1014.
Mahoney et al., Anal. Biochern. (2004) 330:123-129.
Mahoney et at., J. Biol. Chem. (2005) 280:27044-27055.
Mullins et al., Eye (2001) 15:390-395.
Mulloy et al., Carbohydr. Res. (1994) 255:1-26.
Mulloy et al., Thromb. Haemost. (2000) 84:1052-1056.
Mulloy and Forster, Glycobiology (2000)10:1147-1156.
Ostrovsky et at., J. Biol. Chern. (2002) 277:2444-2453.
Pavao et al., J. Biol. Chem. (1995) 270:31027-31036.
Ripoche et at., Biochem J. (1988) 249:593-602.
Saito and Munakata, J. Biochern. (2005) 137:225-233.
Schoberg et al., J. Biol. Chem. (2005) 280:32301-32308.
Schonerr et al., J. Vasc. Res. (2004) 41:499-508.
Seddon et al., JAMA (2004) 291:704-710.
Sim et al., Biosci. Rep (1983) 3:1119-1131.
Sim et al., Methods Enzymot. (1993) 223:13-35.
Thomas et al., Thromb. Haemost. (1984) 52:148-152.
Trouw et al., J. Exp. Med. (2005) 201:1937-1948.
White et al., Protein Sci. (2004) 9:2406-2415.

* cited by examiner

*Primary Examiner*—Lisa V Cook
(74) *Attorney, Agent, or Firm*—Lerner, David, Littenberg, Krumholz & Mentlik, LLP

(57) ABSTRACT

The invention relates to identifying agents which have the ability to preferentially inhibit binding to targets such as heparin of the H384 allotypic variant of human complement Factor H, the allotypic variant associated with age-related macular degeneration (AMD), and the non-disease associated form of the same factor (Y384). The targets of interest show differential binding of the two allotypic variants and antagonists thus identified are of interest in developing treatments for AMD.

14 Claims, 15 Drawing Sheets

US 7,829,301 B2

Figure 1:
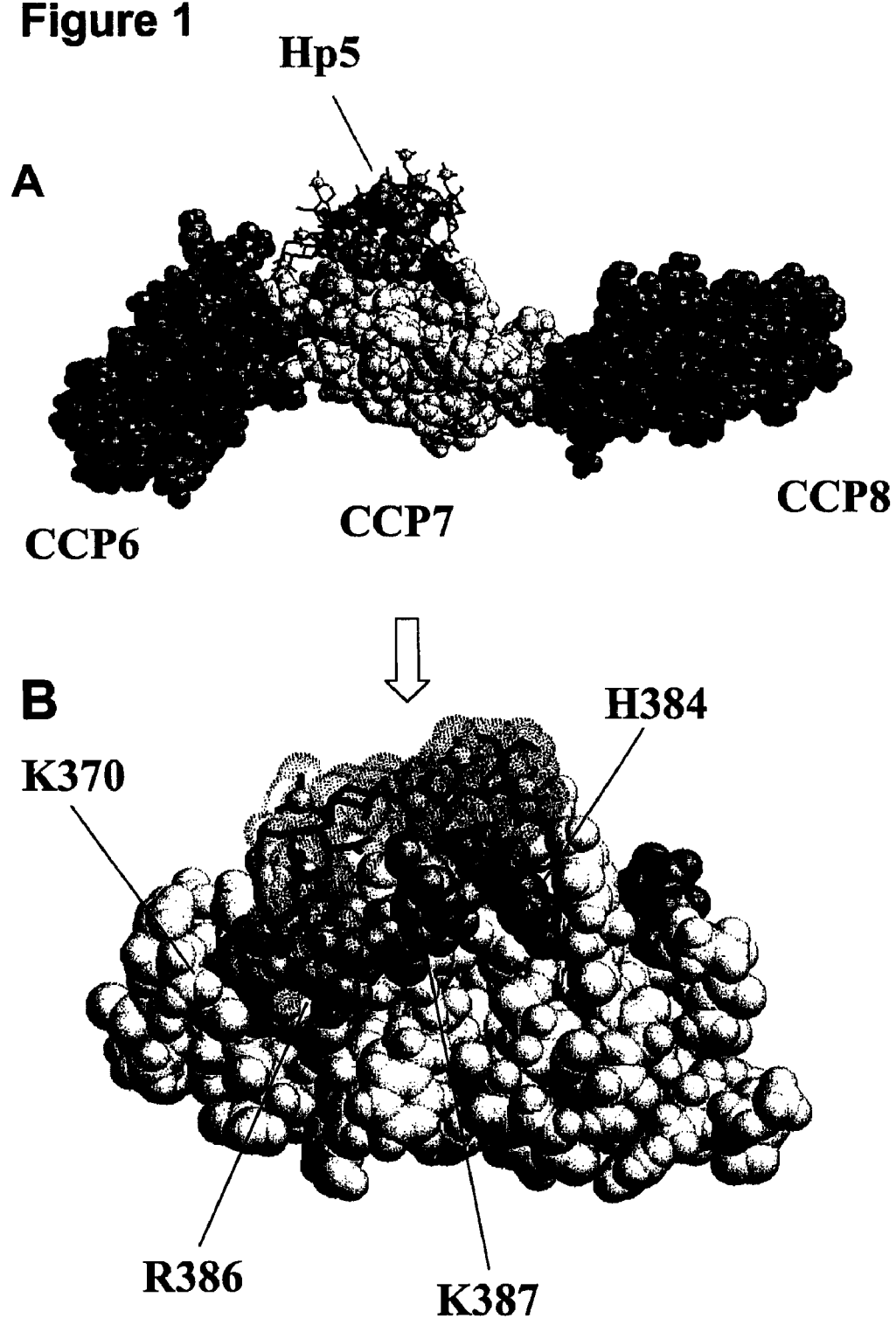
Figure 2:
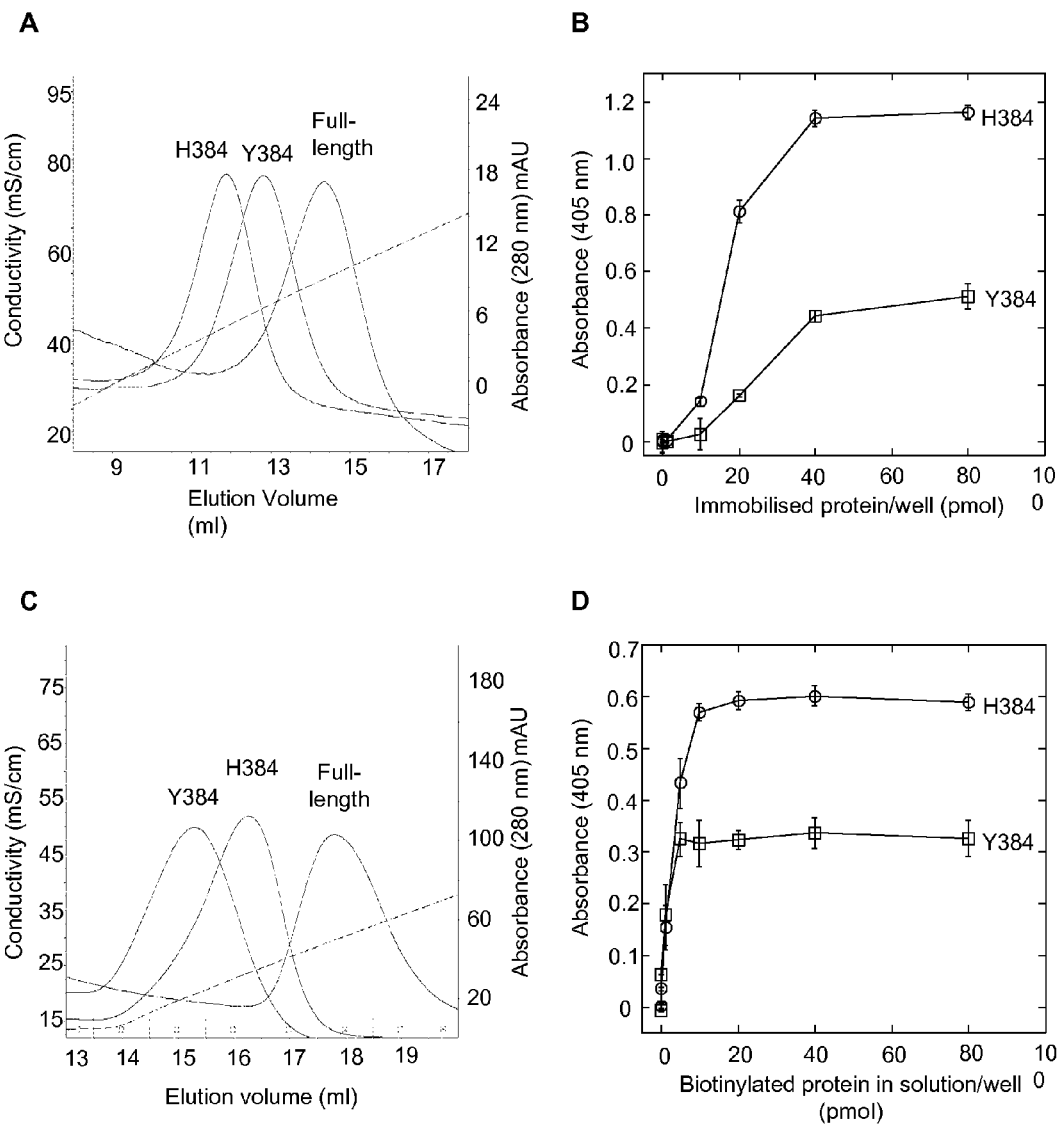

SEQUENCE LISTING

<160> NUMBER OF SEQ ID NOS: 14

<210> SEQ ID NO 1
<211> LENGTH: 188
<212> TYPE: PRT
<213> ORGANISM: Homo sapiens
<220> FEATURE:
<221> NAME/KEY: VARIANT
<222> LOCATION: (1)...(188)
<223> OTHER INFORMATION: Protein sequence of the FHCCP6-8 (H384) construct

<400> SEQUENCE: 1

```
Met Gly Thr Leu Lys Pro Cys Asp Tyr Pro Asp Ile Lys His Gly Gly
  1               5                  10                  15

Leu Tyr His Glu Asn Met Arg Arg Pro Tyr Phe Pro Val Ala Val Gly
             20                  25                  30

Lys Tyr Tyr Ser Tyr Tyr Cys Asp Glu His Phe Glu Thr Pro Ser Gly
         35                  40                  45

Ser Tyr Trp Asp His Ile His Cys Thr Gln Asp Gly Trp Ser Pro Ala
 50                  55                  60

Val Pro Cys Leu Arg Lys Cys Tyr Phe Pro Tyr Leu Glu Asn Gly Tyr
 65                  70                  75                  80

Asn Gln Asn His Gly Arg Lys Phe Val Gln Gly Lys Ser Ile Asp Val
                 85                  90                  95

Ala Cys His Pro Gly Tyr Ala Leu Pro Lys Ala Gln Thr Thr Val Thr
            100                 105                 110

Cys Met Glu Asn Gly Trp Ser Pro Thr Pro Arg Cys Ile Arg Val Lys
        115                 120                 125

Thr Cys Ser Lys Ser Ser Ile Asp Ile Glu Asn Gly Phe Ile Ser Glu
130                 135                 140

Ser Gln Tyr Thr Tyr Ala Leu Lys Glu Lys Ala Lys Tyr Gln Cys Lys
145                 150                 155                 160

Leu Gly Tyr Val Thr Ala Asp Gly Glu Thr Ser Gly Ser Ile Thr Cys
                165                 170                 175

Gly Lys Asp Gly Trp Ser Ala Gln Pro Thr Cys Ile
            180                 185
```

<210> SEQ ID NO 2
<211> LENGTH: 567
<212> TYPE: DNA
<213> ORGANISM: Homo sapiens
<220> FEATURE:
<221> NAME/KEY: allele
<222> LOCATION: (1)...(567)
<223> OTHER INFORMATION: cDNA sequence of the FHCCP6-8 (H384) construct

<400> SEQUENCE: 2

```
atgggtacct tgaaaccttg tgattatcca gacattaaac atggaggtct atatcatgag      60
aatatgcgta gaccatactt tccagtagct gtaggaaaat attactccta ttactgtgat     120
gaacattttg agactccgtc aggaagttac tgggatcaca ttcattgcac acaagatgga     180
tggtcgccag cagtaccatg cctcagaaaa tgttattttc cttatttgga aaatggatat     240
aatcaaaatc atggaagaaa gtttgtacag ggtaaatcta tagacgttgc ctgccatcct     300
ggctacgctc ttccaaaagc gcagaccaca gttacatgta tggagaatgg ctggtctcct     360
actcccagat gcatccgtgt caaaacatgt tccaaatcaa gtatagatat tgagaatggg     420
```

```
tttatttctg aatctcagta tacatatgcc ttaaaagaaa aagcgaaata tcaatgcaaa      480
ctaggatatg taacagcaga tggtgaaaca tcaggatcaa ttacatgtgg gaaagatgga      540
tggtcagctc aacccacgtg catttaa                                          567
```

```
<210> SEQ ID NO 3
<211> LENGTH: 188
<212> TYPE: PRT
<213> ORGANISM: Homo sapiens
<220> FEATURE:
<221> NAME/KEY: VARIANT
<222> LOCATION: (1)...(188)
<223> OTHER INFORMATION: FHCCP6-8 (Y384 allotype of mature Factor H)

<400> SEQUENCE: 3
```

```
Met Gly Thr Leu Lys Pro Cys Asp Tyr Pro Asp Ile Lys His Gly Gly
 1               5                   10                  15

Leu Tyr His Glu Asn Met Arg Arg Pro Tyr Phe Pro Val Ala Val Gly
            20                  25                  30

Lys Tyr Tyr Ser Tyr Tyr Cys Asp Glu His Phe Glu Thr Pro Ser Gly
        35                  40                  45

Ser Tyr Trp Asp His Ile His Cys Thr Gln Asp Gly Trp Ser Pro Ala
    50                  55                  60

Val Pro Cys Leu Arg Lys Cys Tyr Phe Pro Tyr Leu Glu Asn Gly Tyr
65                  70                  75                  80

Asn Gln Asn Tyr Gly Arg Lys Phe Val Gln Gly Lys Ser Ile Asp Val
                85                  90                  95

Ala Cys His Pro Gly Tyr Ala Leu Pro Lys Ala Gln Thr Thr Val Thr
            100                 105                 110

Cys Met Glu Asn Gly Trp Ser Pro Thr Pro Arg Cys Ile Arg Val Lys
        115                 120                 125

Thr Cys Ser Lys Ser Ser Ile Asp Ile Glu Asn Gly Phe Ile Ser Glu
    130                 135                 140

Ser Gln Tyr Thr Tyr Ala Leu Lys Glu Lys Ala Lys Tyr Gln Cys Lys
145                 150                 155                 160

Leu Gly Tyr Val Thr Ala Asp Gly Glu Thr Ser Gly Ser Ile Thr Cys
                165                 170                 175

Gly Lys Asp Gly Trp Ser Ala Gln Pro Thr Cys Ile
            180                 185
```

```
<210> SEQ ID NO 4
<211> LENGTH: 567
<212> TYPE: DNA
<213> ORGANISM: Homo sapiens
<220> FEATURE:
<221> NAME/KEY: allele
<222> LOCATION: (1)...(567)
<223> OTHER INFORMATION: cDNA sequence of the FHCCP6-8 Y384 allotype of
      mature Factor H

<400> SEQUENCE: 4
```

```
atgggtacct tgaaaccttg tgattatcca gacattaaac atggaggtct atatcatgag      60
aatatgcgta gaccatactt tccagtagct gtaggaaaat attactccta ttactgtgat     120
gaacattttg agactccgtc aggaagttac tgggatcaca ttcattgcac acaagatgga     180
tggtcgccag cagtaccatg cctcagaaaa tgttattttc cttatttgga aaatggatat     240
aatcaaaatt atggaagaaa gtttgtacag ggtaaatcta tagacgttgc ctgccatcct     300
ggctacgctc ttccaaaagc gcagaccaca gttacatgta tggagaatgg ctggtctcct     360
```

```
actcccagat gcatccgtgt caaaacatgt tccaaatcaa gtatagatat tgagaatggg    420
tttatttctg aatctcagta tacatatgcc ttaaaagaaa aagcgaaata tcaatgcaaa    480
ctaggatatg taacagcaga tggtgaaaca tcaggatcaa ttacatgtgg gaaagatgga    540
tggtcagctc aacccacgtg catttaa                                        567
```

```
<210> SEQ ID NO 5
<211> LENGTH: 39
<212> TYPE: DNA
<213> ORGANISM: Artificial Sequence
<220> FEATURE:
<223> OTHER INFORMATION: Construct primer FHCCP6-8 S

<400> SEQUENCE: 5
aattaaatcc atgggtacct tgaaaccttg tgattatcc                            39

<210> SEQ ID NO 6
<211> LENGTH: 31
<212> TYPE: DNA
<213> ORGANISM: Artificial Sequence
<220> FEATURE:
<223> OTHER INFORMATION: Construct primer FHCCP6-8 AS

<400> SEQUENCE: 6
aaggatcctt aaatgcacgt gggttgagct g                                    31

<210> SEQ ID NO 7
<211> LENGTH: 36
<212> TYPE: DNA
<213> ORGANISM: Artificial Sequence
<220> FEATURE:
<223> OTHER INFORMATION: Mutational primer H384Y S

<400> SEQUENCE: 7
ggatataatc aaaattatga agaaagtttg tacagg                               36

<210> SEQ ID NO 8
<211> LENGTH: 37
<212> TYPE: DNA
<213> ORGANISM: Artificial Sequence
<220> FEATURE:
<223> OTHER INFORMATION: Mutational primer H384Y AS

<400> SEQUENCE: 8
cctatattag ttttagtacc ttctttcaaa catgtcc                              37

<210> SEQ ID NO 9
<211> LENGTH: 41
<212> TYPE: DNA
<213> ORGANISM: Artificial Sequence
<220> FEATURE:
<223> OTHER INFORMATION: Mutational primer K370A S

<400> SEQUENCE: 9
cagcagtacc atgcctcaga gcatgttatt ttccttattt g                         41

<210> SEQ ID NO 10
<211> LENGTH: 41
<212> TYPE: DNA
<213> ORGANISM: Artificial Sequence
<220> FEATURE:
<223> OTHER INFORMATION: Mutational primer K370A AS

<400> SEQUENCE: 10
gtcgtcatgg tacggagtct cgtacaataa aaggaataaa c                         41
```

```
<210> SEQ ID NO 11
<211> LENGTH: 44
<212> TYPE: DNA
<213> ORGANISM: Artificial Sequence
<220> FEATURE:
<223> OTHER INFORMATION: Mutational primer R386A S

<400> SEQUENCE: 11
ggatataatc aaaatcatgg agcaaagttt gtacagggta aatc                 44

<210> SEQ ID NO 12
<211> LENGTH: 44
<212> TYPE: DNA
<213> ORGANISM: Artificial Sequence
<220> FEATURE:
<223> OTHER INFORMATION: Mutational primer R386A AS

<400> SEQUENCE: 12
cctatattag ttttagtacc tcgtttcaaa catgtcccat ttag                 44

<210> SEQ ID NO 13
<211> LENGTH: 47
<212> TYPE: DNA
<213> ORGANISM: Artificial Sequence
<220> FEATURE:
<223> OTHER INFORMATION: Mutational primer K387A S

<400> SEQUENCE: 13
gatataatca aaatcatgga agagcgttgt acagggtaaa tctatag              47

<210> SEQ ID NO 14
<211> LENGTH: 48
<212> TYPE: DNA
<213> ORGANISM: Artificial Sequence
<220> FEATURE:
<223> OTHER INFORMATION: Mutational primer K387A AS

<400> SEQUENCE: 14
ctatattagt tttagtacct tctcgcaaac atgtcccatt tagatatc              48
```

SCREENING ASSAYS FOR BINDING ANTAGONISTS OF THE AMD-ASSOCIATED VARIANT OF FACTOR H (H384)

CROSS-REFERENCE TO RELATED APPLICATIONS

This application claims priority from U.S. provisional application 60/838,770 filed Aug. 18, 2006. The contents of this document are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 255352002200Seqlist.txt | Nov. 29, 2007 | 7,494 bytes |

FIELD OF THE INVENTION

The present invention provides assays for identifying antagonists which preferentially inhibit binding of the H384 allotypic variant of human complement Factor H associated with age-related macular degeneration (AMD) compared to the non-disease-associated form of the same protein (Y384), where the two variants show differential binding to the binding target. Such antagonists are of especial interest in relation to developing treatments for AMD.

BACKGROUND OF THE INVENTION

In the Western World, AMD is the leading cause of natural blindness in the elderly affecting 50 million individuals worldwide and its prevalence may become greater with an increasingly elderly population. AMD manifests itself by the progressive destruction of the macula causing central vision loss. The dry form of AMD, which accounts for 90% of cases, is associated with the presence of small yellow 'drusen' deposits between the choroid and the retinal pigment epithelium that result in gradual vision loss. About 10-20% of patients with dry AMD go on to develop the more severe wet form. Recently, a common allelic variant of human complement Factor H (FH) has been linked to an increased risk of developing dry AMD (Day et al. (1998) Immunogenetics 27, 211-214; Klein et al. (2005) Science 308, 385-389; Haines et al. (2005) Science 308, 419-421; Edwards et al. (2005) Science 308, 421-424). This variant arises from a tyrosine/histidine polymorphism at amino acid residue 384 in the mature protein (referred to as residue 402 in some of the references above; corresponding to the T1277C polymorphism in the FH gene). About 35% of the individuals of European descent carry the disease-associated H384 allele, which increases the likelihood of developing AMD by 2.7 fold and may account for 50% of the attributable risk of AMD. In individuals who are homozygous for the risk allele, the likelihood of AMD is increased by a factor of 7.4. Recently, the H384 allele has also been associated with an increased risk of myocardial infarction and it has been suggested that atherosclerosis could contribute to macular degeneration (Kardys et al. (2006) J. Am. Coll. Cardiol. 47, 1568-1575). Interestingly, FH deficiency is also associated with type II membraneoproliferative glomerulonephritis (MPGN II), a rare renal disease, in which drusen have a similar composition to those found in AMD (Mullins et al. (2001) Eye 15, 390-395).

Factor H is a 155-kDa plasma protein that acts as a cofactor for the breakdown of complement C3b by Factor I. It is composed of 20 Complement Control Protein (CCP; also termed short consensus repeats or SCR) modules, each of approximately 60 amino acids with a compact structure. The Y384H polymorphism is located within CCP7. Factor H is believed to discriminate self from non-self by recognizing polyanionic structures on the former, such as sialic acid and the glycosaminoglycan (GAG) chains of proteoglycans (e.g., heparan sulphate (HS) and dermatan sulphate (DS)), and thus inhibit complement activation on host surfaces. Factor H has been shown to be present in retinal blood vessels in the choroid and is associated with the drusen of AMD patients. In addition, markers of complement activation (e.g. C5b-9 and C3 fragments, including iC3b) have been detected in the Bruch's membrane and drusen of AMD patients, leading to the hypothesis that AMD results from an aberrant inflammatory process that includes inappropriate complement activation. Furthermore, it has been reported that the glycosaminoglycan heparan sulphate is present in the macula of AMD patients but not detectable in controls (Kliffen et al. (1996) Arch. Opthalmol. 114, 1009-1014).

Using a recombinant protein composed of CCPs 6-8 (including an additional N-terminal non-authentic glycine at the beginning of the Factor H derived sequence (see FIG. 7); hereinafter referred to as FHCCP6-8), we have now shown that amino acid residue 384 of Factor H is adjacent to a heparin-binding site in CCP7. Furthermore, we have shown that the AMD-associated H384 allotypic variant and the Y384 non-disease associated variant of Factor H exhibit differential binding to various targets, e.g. notably the H384 allotypic variant has been shown, for example, to bind better to a sample of the well-characterised 4th International Standard (4IS) heparin. It is thus now extrapolated that substitution of histidine for tyrosine at position 384 of mature Factor H may affect binding of Factor H in vivo to polyanionic patterns on host surfaces, potentially influencing complement activation, immune complex clearance and inflammation in the macula of AMD patients. More particularly, we postulate that the H384 allotype of Factor H may be preventing appropriate complement activation on or near to drusen by its binding to heparin-like structures thus leading to impairment in the clearance of drusen. It follows that there is a wish to identify agents which will inhibit binding of the H384 allotype of Factor H to heparin and other binding targets while not preventing the function of the Y384 allotype of that protein.

SUMMARY OF THE INVENTION

The present invention thus provides a method of identifying whether a test agent has the ability to preferentially inhibit binding of the H384 allotypic variant of Factor H to a target compared with the Y384 allotypic variant of that factor, said method comprising:
  (i) providing a target to which both said variants of Factor H will bind differentially;
  (ii) contacting said target, both in the presence and absence of the test agent, with each of said variants, or a recombinant protein presenting a target-binding fragment of each of said variants including amino acid residue 384 and capable of heparin binding via the heparin-binding residues of the Complement Control Protein module 7(CCP7), under conditions whereby both variant proteins employed bind said target differentially in the absence of the test agent, and (iii) determining whether the test agent exhibits said ability;

with the proviso that where the target provided is heparin it exhibits higher binding of the H384 variant protein employed than the Y384 variant protein employed in the absence of the test agent.

A preferred target-binding fragment of Factor H for use in such screening assays is Complement Control Protein Modules 6-8 or a fragment thereof which retains heparin binding ability. As indicated above, such a Factor H fragment may be provided as a recombinant protein which binds heparin via the heparin-binding residues of the CCP7 module.

The inventors have identified a number of targets for use in screening assays of the invention. These include heparan sulphate (HS), e.g. bovine kidney heparan sulphate, dermatan sulphate (DS), C-reactive protein (CRP) or a CCP6-8 binding portion thereof, DNA, the extracellular matrix proteoglycan fibromodulin (FMOD), either glycosylated or preferably lacking some glycosylation, or a CCP6-8 binding portion thereof, or necrotic cells. Each of these targets is able to differentially bind the Y384 and H384 variants of Factor H.

CRP is a known activator of the classical pathway of complement and also binds to the CCP7 region of FH (Giannakis et al. (2003) Eur. J. Immunol. 33, 962-969; Jarva et al. (1999) J. Immunol. 163, 3957-3962). It is implicated in AMD since circulating CRP levels have been found to be higher in AMD patients (Seddon et al. (2004) JAMA 291, 704-710). Again using recombinant FHCCP6-8 proteins, we have shown that the H384 variant binds CRP poorly compared to the Y384 variant.

Using a direct binding assay, we have also shown that recombinant FHCCP6-8 interacts with the polypeptide of FMOD and not its glycosaminoglycan modifications and that the Y384 variant of CCP6-8 also binds to this target better than the H384 form. FMOD is a member of the leucine-rich repeat (LRR) protein family and was first described as a 59 kDa protein bound to collagen fibres in cartilage. The extracellular matrix of the eye shares a number of structural components with hyaline cartilage. Fibromodulin is found in sclera and it is expressed by epithelial cells of the eye (Schonerr et al. (2004) J. Vasc. Res. 41, 499-508). FMOD often contains one or two polyanionic keratan sulphate chains, distributed among the four potential substitution sites that are present in the leucine-rich region. An additional anionic domain is in the N-terminal region, containing up to nine tyrosine sulphate residues. It was previously reported that FMOD binds C1q, which leads to complement activation (Sjöberg et al. (2005) J. Biol. Chem. 280, 32301-32308). FMOD also binds FH causing inhibition of the alternative pathway and thus a decrease in MAC formation (Sjöberg et al. (2005) ibid). In the latter case, it is not clear which parts of the two molecules are involved in the interaction, although binding to C1q and FH, respectively, appears to engage different sites on FMOD.

We have additionally found that recombinant FHCCP6-8 is able to interact with both DNA, more particularly linearized pcDNA3 plasmid DNA, and necrotic cells but, in contrast with binding to CRP and FMOD, the H384 variant binds these targets more strongly than the Y384 variant, i.e. similar to the finding with 4IS heparin. DNA is able to activate human complement. It was previously shown that complement inhibitor C4b-binding protein (C4BP) interacts with DNA and that there is more complement activation in human serum depleted of C4BP than in normal serum when DNA is added (Trouw et al. (2005) J. Exp. Med. 201, 1937-1948). In the case of C4BP, DNA may be one ligand attaching this inhibitor to necrotic cells. FH binds DNA (Gardner et al. (1980) Biochem. Biophys. Res. Commun. 94, 61-67) and possibly functions in a similar way. At present the molecular mechanism underlying the DNA-FH interaction is not clear. It is, however, plausible that there are multiple interaction sites in FH for DNA as has been observed for many other FH ligands. It is now apparent that at least one of the DNA binding sites is localized to CCP6-8, probably within CCP7. It is possible that enhanced binding of the H384 allotypic variant of FH to DNA exposed on necrotic cells present in drusen could lead to reduced complement-mediated opsonisation, giving rise to impaired phagocytosis.

Late apoptotic and necrotic cells bind C1q and are able to activate complement to some extent. Previously, it has been proposed that these cells also capture complement inhibitor C4b-binding protein in order to allow phagocytosis of dying cells via C1q and C3b receptors but limiting inflammation. Furthermore, FH is known to be able to interact with dying cells (Elward et al. (2005) J. Biol. Chem. 280, 36342-36354) but the molecular site of interaction has not previously been defined. By rendering Jurkat T cells necrotic and analyzing the binding of FHCCP6-8(H384) and FHCCP6-8(Y384) variants by flow cytometry, we have shown that at the concentration of 10 μg/ml the H384 variant binds necrotic cells better than the Y384 variant. It appears therefore that the H384 disease-associated allotype of FH is likely to accumulate on necrotic cells at higher concentrations than the Y384 allotype, which may lead to increased inhibition of complement, thus reducing complement-mediated phagocytosis of necrotic debris.

It is thus postulated that variations in binding affinity of the H384 and Y384 variants of Factor H in vivo mean that complement activation in response to different targets will differ between His/His homozygotes and Tyr/Tyr homozygotes. Thus the AMD-associated H384 allotype may provide insufficient complement down regulation when CRP is the activator, but excessive down regulation on ligands such as DNA and necrotic cells leading to impaired phagocytosis of cell debris. All such interactions could contribute to AMD disease progression either via increased complement activation and resulting inflammation or through favouring accumulation of drusen (which contain cell debris and immune complexes).

It is most preferred that the target is a heparin. The skilled artisan will appreciate that there are many different forms of heparin. For instance forms vary due to the length of the oligosaccharide and the nature of sugar monomers. In subjects with AMD, the inventors (as discussed above) have realised that H384 variant of Factor H binds with greater affinity than the Y384 variant to heparin components of the extracellular matrix. Accordingly the above-noted proviso in the method of the invention. When the target is a heparin it is preferably an international standard of heparin, e.g. the 4th or 5th International Standard (4IS or 5IS).

BRIEF DESCRIPTION OF THE DRAWINGS

FIG. 1A-B: Prediction of heparin-binding site on CCP7 of Factor H. In the top panel (A), predictions are shown for heparin pentasaccharides docked onto a model of CCP7, where CCP modules 6 and 8 (grey) were also included in the calculations; the 5 lowest energy complexes are illustrated. Basic amino acids potentially involved in binding and residue 384 (His variant) are indicated; scattering and analytical ultracentrifugation experiments on FHCCP6-8(H384) indicate these are likely to be on an accessible face of CCP7. In the lower panel (B), the lowest energy CCP7/heparin model is shown. The binding of heparin to the H384/Y384 allotypic variants reveal that these have similar pH dependencies, indicating that a histidine residue is likely to be involved in the interaction.

FIG. 2A-D: Comparison of heparin-binding properties for histidine and tyrosine variants of Factor H. (A,C) FHCCP6-8(H384), FHCCP6-8(Y384) and full-length Factor H were analyzed by heparin-affinity chromatography at pH 7.3 on either a HiTrap heparin column (A) or a home-made column in which heparin (4IS) had been coupled to CNBr-activated Sepharose (C). The proteins were eluted with a linear NaCl gradient, where dashed and solid lines show the conductivity of eluent and absorbance, respectively. In the case of the FHCCP6-8H is/Tyr constructs all the protein adhered to the columns, whereas with full-length Factor H a small amount of a 155 kDa-species was present in the flow-through (3-5% of protein loaded), as determined by SDS-PAGE. (B,D) Analysis of FHCCP6-8(H384) and FHCCP6-8(Y384) proteins by microtitre plate assays (circles and squares, respectively). (B) Binding of biotinylated heparin (4IS) to immobilized FHCCP6-8(H384) and FHCCP6-8(Y384) proteins. (D) Interaction of biotinylated-FHCCP6-8(H384/Y384) proteins with immobilized heparin (4IS). In (B/D), values are plotted as mean absorbance (n=8)±S.E. All data are representative of at least two independent experiments.

Figure 3:
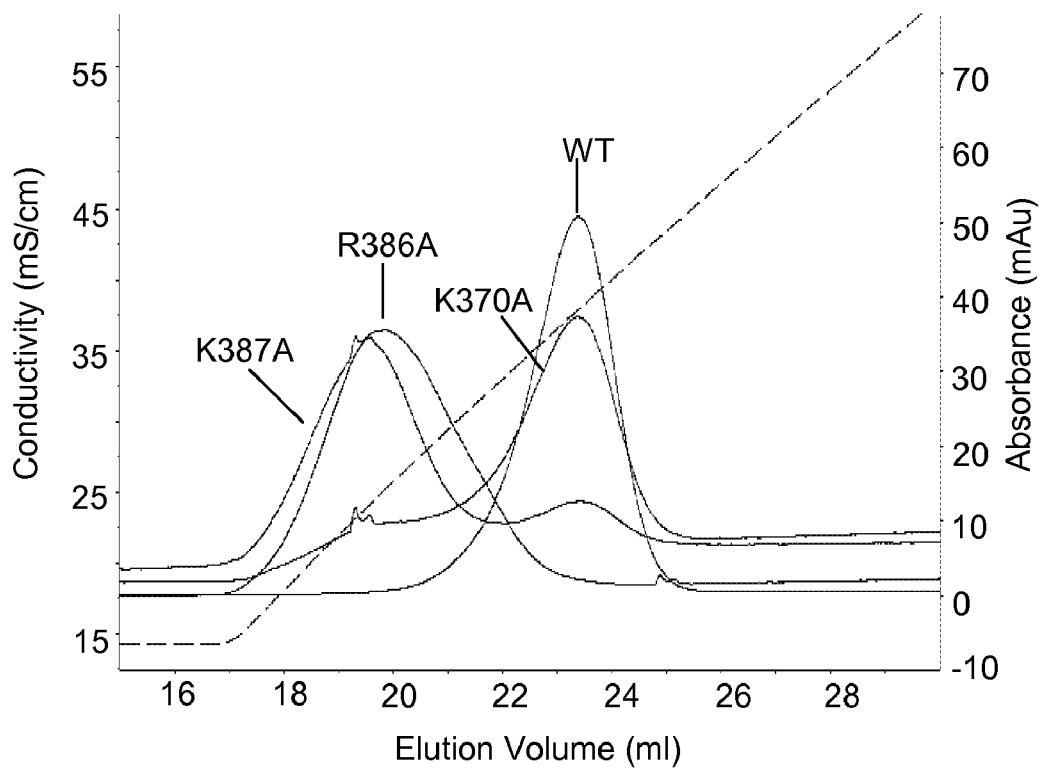
Figure 3:
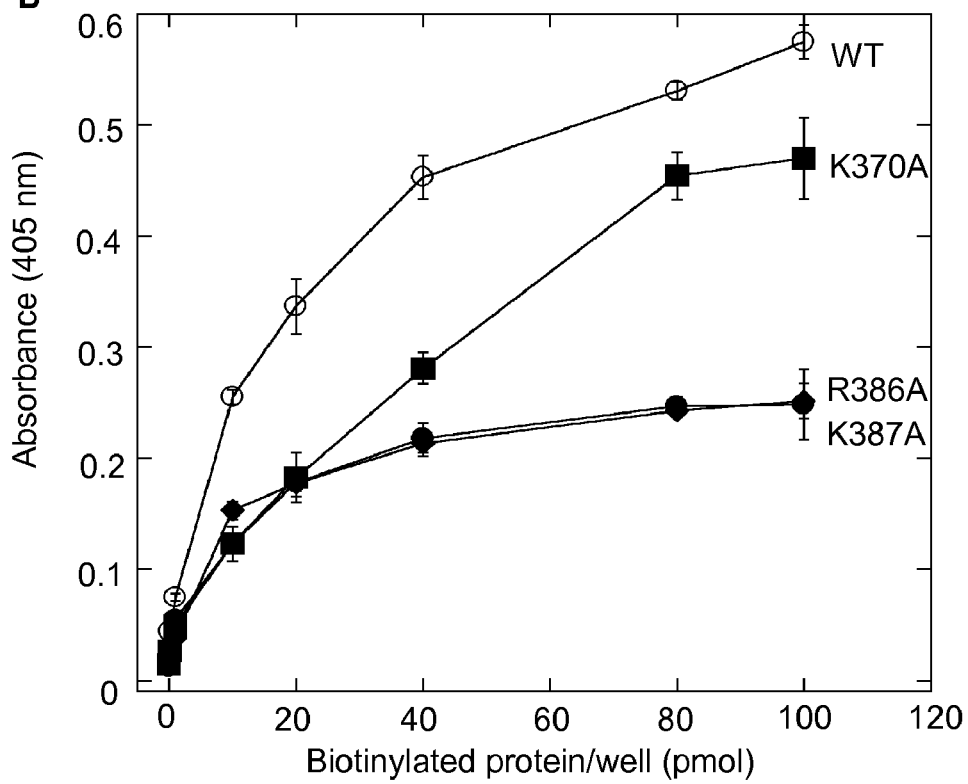

FIG. 3A-B: Effect of mutagenesis on heparin-binding properties of Factor H (H384). Mutants K370A (squares), R386A (diamond) and K387A (circle) were compared to wild-type protein by (A) affinity chromatography on a HiTrap heparin column and (B) a microtitre plate assay where the binding of biotinylated-heparin (4IS) to immobilized wild-type (WT) and mutant FHCCP6-8(H384) proteins was determined. In (A) the absorbance at 280 nm and the conductivity are shown and the chromatogram is a representative example of three independent experiments. In (B) all values are plotted as mean absorbance (n=8)±S.E.

FIG. 4A-B: Effect of selective desulphation on the binding of heparin to the histidine and tyrosine variants of factor H. The interaction of biotinylated-FHCCP6-8(H384) (A) and biotinylated-FHCCP6-8(Y384) (B) with immobilized 2IS heparin that has been untreated or selectively desulphated: 2-O-desulphated (2-O deS), 6-O-desulphated (6-O deS), 2,6-O-desulphated (2,6-O deS), N-desulphated (N deS), N-desulphated, re-N-acetylated (N deS, re N Ac). All values are plotted as mean absorbance (n=8)±S.E.

FIG. 5A-C: Heparin and HS-binding activities of FHCCP6-8(H384), FHCCP6-8(Y384) and the full-length Factor H. The binding of full-length Factor H (A), FHCCP6-8(H384) (B) and FHCCP6-8(Y384) (C) to 4IS (circles), HSI (squares) or HSII (diamonds), was determined, where these GAGs were immobilized on microtitre plates plasma polymerized with allylamine. HSI and HSII were derived from a GAG-rich pig mucosal fraction; the HSI has a lower level of sulphation than HSII. All values are plotted as mean absorbance (n=8)±S.E.

Figure 6:
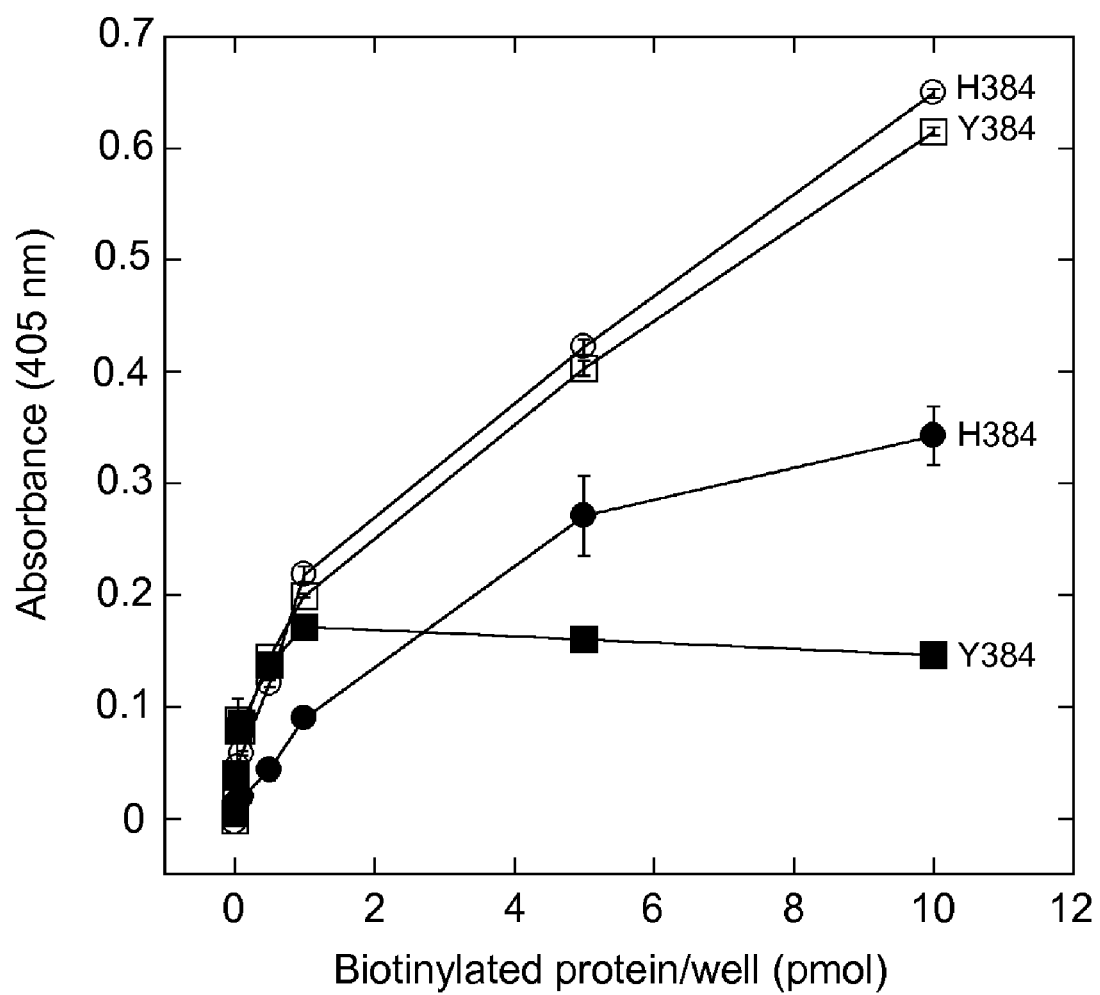

FIG. 6: The DS-binding activities of the histidine and tyrosine variants of Factor H. The interaction of biotinylated-FHCCP6-8(H384) and biotinylated-FHCCP6-8(Y384) proteins (circles and squares, respectively) with immobilized DS (solid symbols) compared to LMr heparin (open symbols). In these experiments the biotinylated proteins were investigated at 0-10 pmol/well (i.e., suboptimal for the heparin signal) to allow an accurate binding curve to be determined with DS; LMr heparin was used as a control since the H384/Y384 proteins have essentially identical binding activities to this GAG over the concentration range studied. All values are plotted as mean absorbance (n=8)±S.E.

Figure 7:
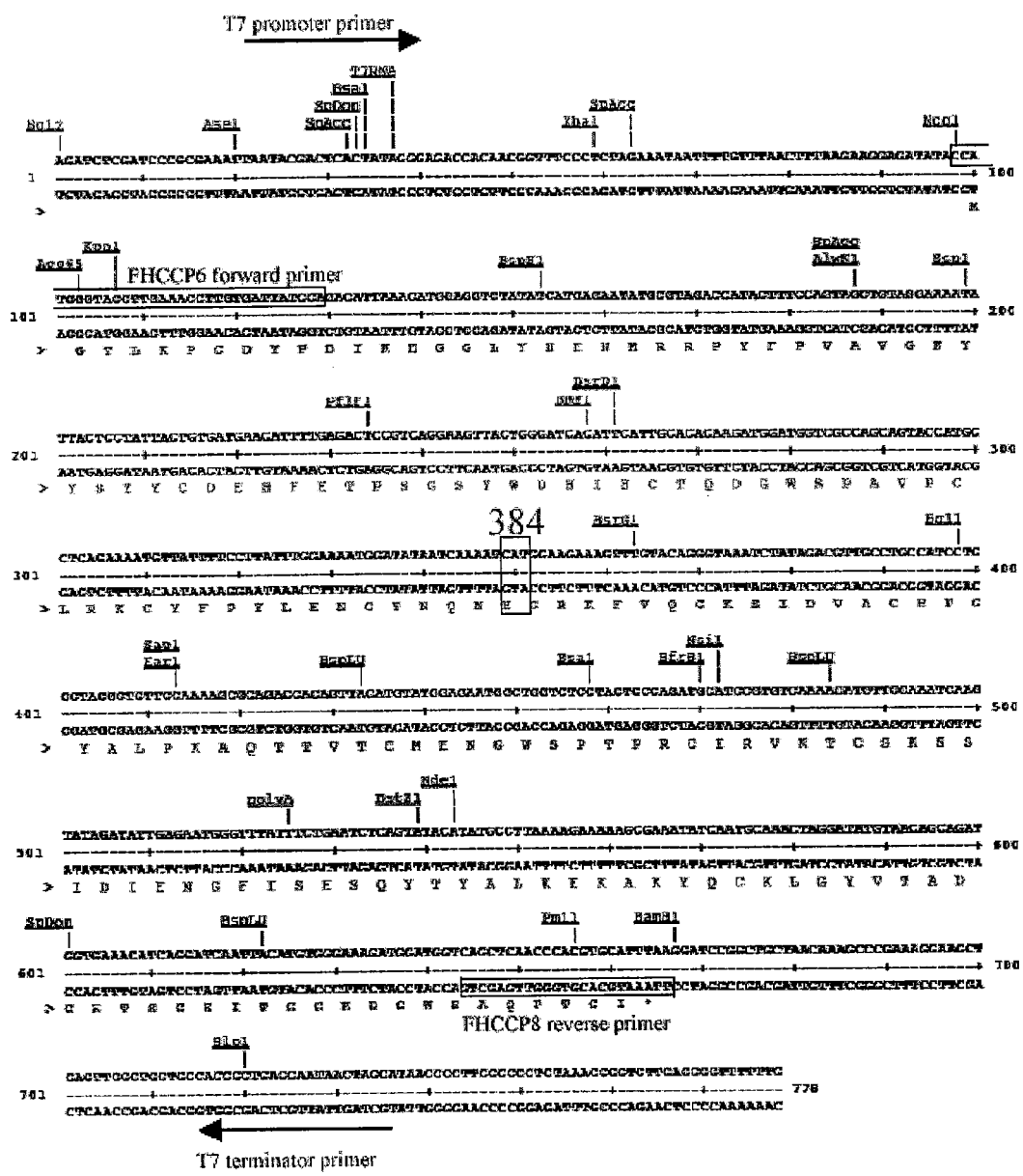

FIG. 7: The cDNA and protein sequences (SEQ ID NOS: 1-2) of the FHCCP6-8(H384) construct. The positions of the primers used to amplify the FHCCP6-8 sequence, the NcoI and BamHI restriction sites used in inserting the PCR product into the pET14-b vector cloning cassette, and the T7 promoter/terminator primers used in sequencing are indicated. The protein product includes a methionine and a non-authentic glycine at the beginning of the FHCCP6-8H is sequence resulting from engineering of the NcoI restriction site. The position of the H384 codon is shown (see also Table 2 below).

FIG. 8A-D: The binding of FHCCP6-8(H384) and FHCCP6-8(Y384) to different heparin preparations. The binding of biotinylated-H384/Y384 proteins to (A) 5IS heparin, (B) low molecular weight (LMr) heparin, (C) enoxaparin and (D) dalteparin immobilized on EpranEx plates. All values are plotted as mean absorbance (n=8)±S.E.

Figure 9:
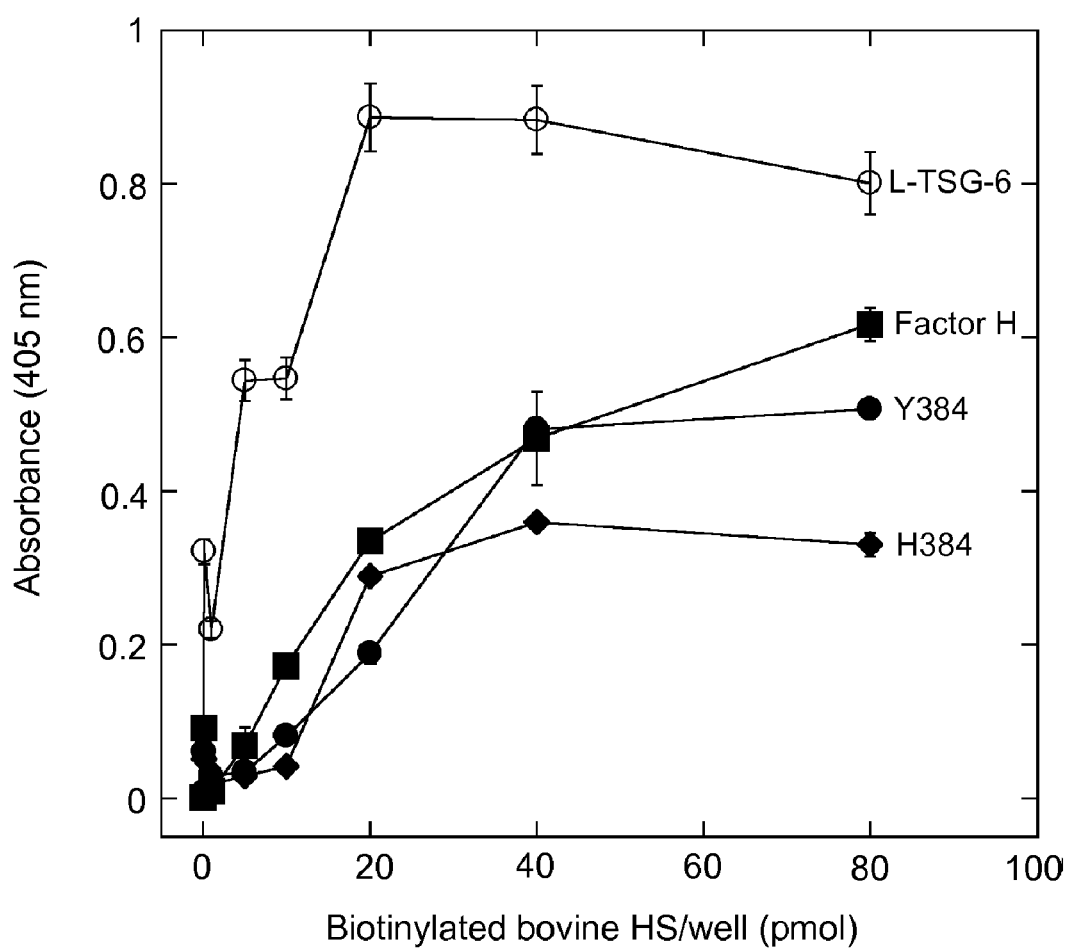

FIG. 9: Binding of immobilized full length Factor H, FHCCP6-8(H384) and FHCCP6-8(Y384) to biotinylated bovine kidney heparan sulphate. Immobilized full length Factor H (■), FHCCP6-8(H384) (♦) and FHCCP6-8(Y384) (●) all interact with biotinylated bovine kidney HS. The positive control for HS binding, immobilized Link-TSG6 (L-TSG-6; ○) is also shown. All values are plotted as mean absorbance (n=8)±S.E.

Figure 10:
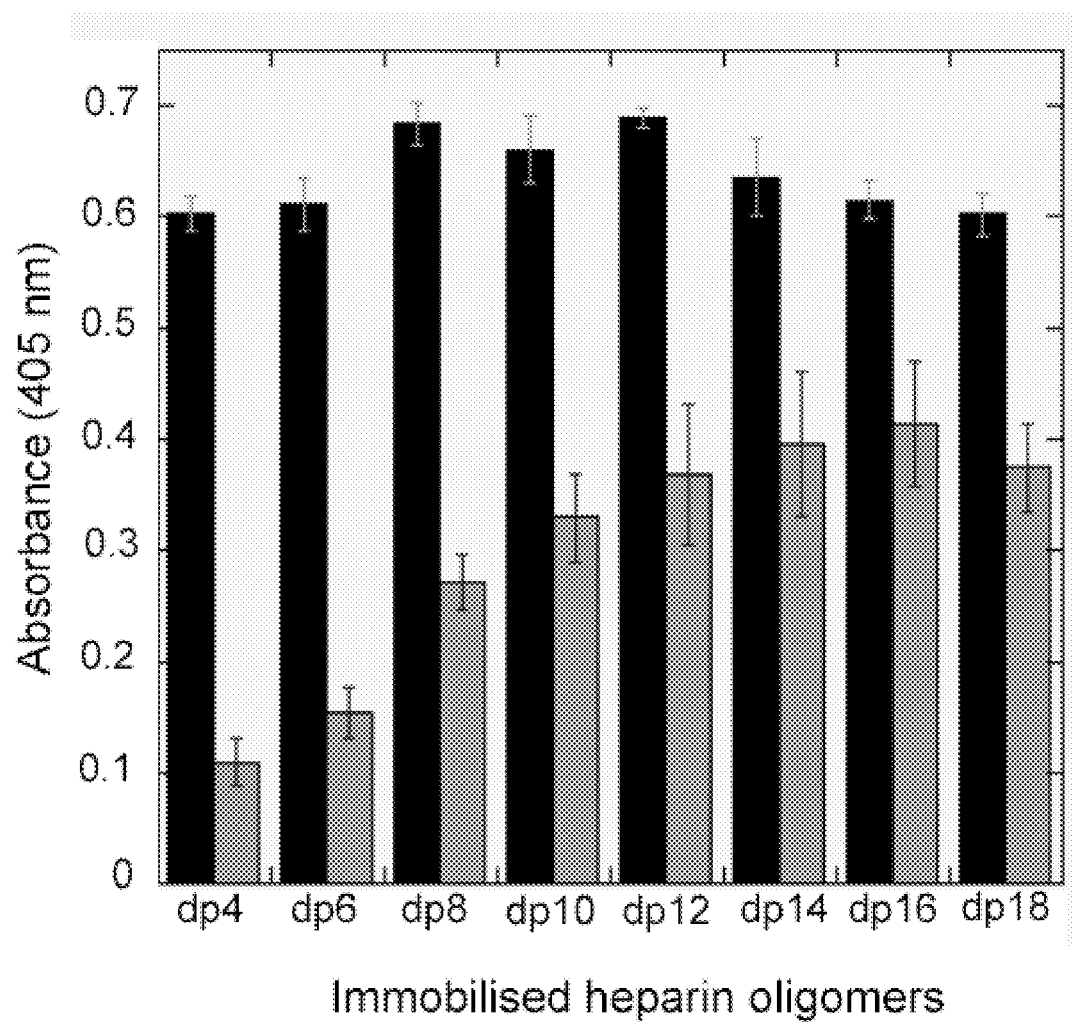

FIG. 10: Comparisons of the interactions of FHCCP6-8 (H384) and the corresponding Y384 variant with heparin oligomers of different lengths. The binding of biotinylated-FHCCP6-8(H384) (black bars) or biotinylated-FHCCP6-8 (Y384) (grey bars) to heparin oligosaccharides (dp4 to dp18) immobilized on microtitre plates plasma polymerized with allylamine. All values are plotted as mean absorbance values (n=8)±S.E.

Figure 11:
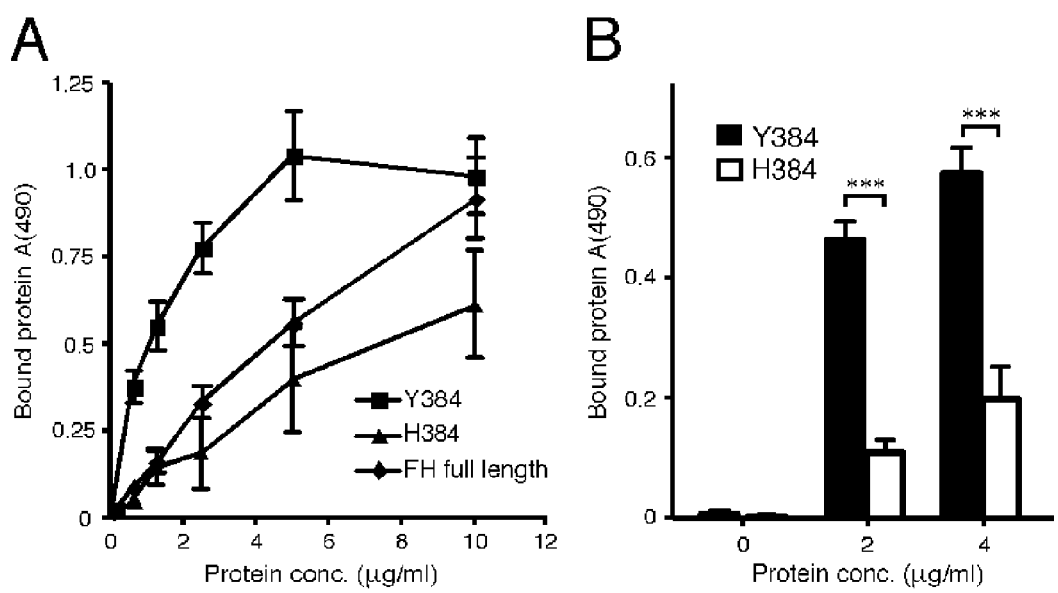

FIG. 11A-B: Binding of the H384 variant and Y384 variant of FHCCP6-8 to CRP. A. CRP was coated onto microtitre plate wells and the binding of varying concentrations of either FHCCP6-8 (H384), FHCCP6-8 (Y384) or full length FH was determined. Bound proteins were detected with a FH-specific polyclonal antibody. B. CRP was immobilized onto microtitre plate wells and biotinylated FHCCP6-8 variants were incubated at two different concentrations. Bound protein was detected with a streptavidin peroxidase kit. Background signal was subtracted from the original values. The figures show representative experiments performed in triplicate. The data are shown as mean values (n=3)±standard deviation and in B asterisks indicate significance accordingly: ***, $p<0.001$.

FIG. 12A-C: Binding of FHCCP6-8(H384), FHCCP6-8 (Y384) and full length FH to FMOD. A. FMOD was coated in microtitre plate wells at a concentration of 10 μg/ml. BSA was used as the negative coating control. FHCCP6-8(H384) and FHCCP6-8(Y384) recombinant proteins or full length FH were incubated in fluid phase and bound protein was detected with a specific polyclonal antibody. B. FMOD was coated in microtitre plate wells as described for A. Biotinylated versions of FHCCP6-8(H384) and FHCCP6-8(Y384) were incubated in the wells and bound protein was detected with a streptavidin peroxidase kit. C. Untreated (glycosylated) and N-glycosidase F-treated FMOD were assessed for binding full length FH in a microtitre plate based binding assay. Bound protein was detected with a specific polyclonal antibody. For the results presented in A and B background signal was subtracted from the original values. The figures show representative experiments performed in triplicate. The data are shown as mean values (n=3)±standard deviation and in B asterisks indicate significance accordingly: , p<0.01; *, p<0.001.

Figure 13:
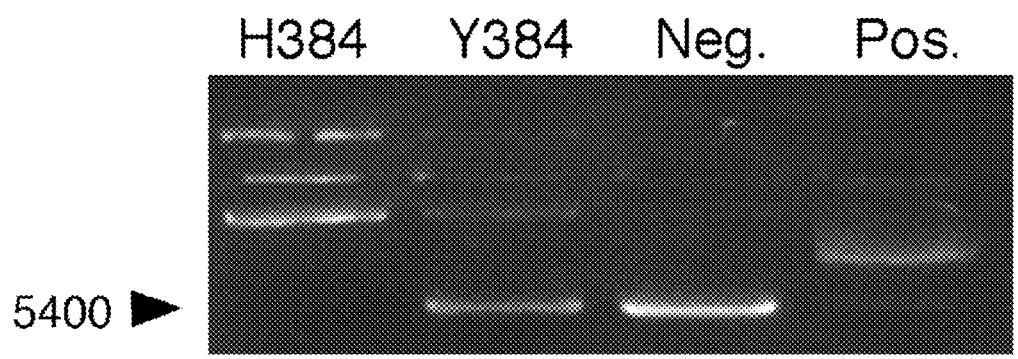

FIG. 13: Differential binding of FHCCP6-8(H384) and FHCCP6-8(Y384) to DNA. Linearized pcDNA3 vector DNA was incubated in solution with either FHCCP6-8 variant or full length FH at 37° C. for 30 minutes. The samples were run in an agarose gel containing ethidium bromide and the DNA was detected with UV light. The figure shows a representative, reproducible experiment. The arrowhead indicates the size of uncomplexed linearized vector.

Figure 14:
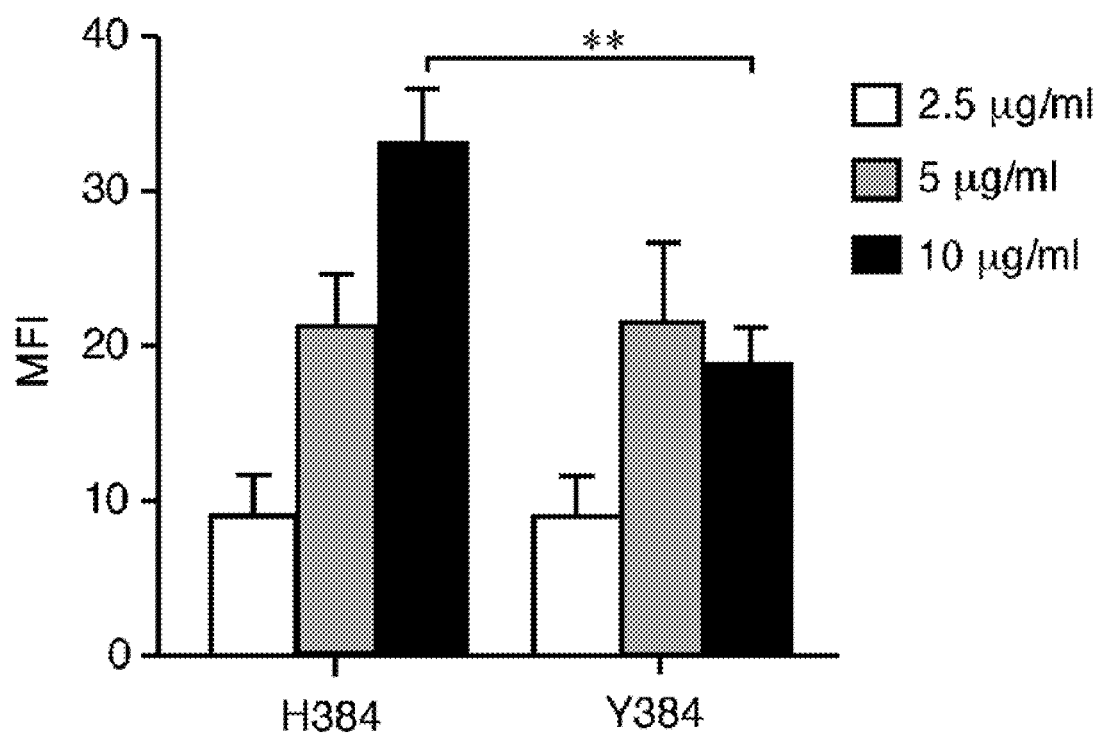

FIG. 14: Differential binding of FHCCP6-8(H384) and FHCCP6-8(Y384) to necrotic cells. Jurkat-T cells were rendered necrotic by heat and incubated with varrying concentrations of both FH variants: white columns 2.5 µg/ml; grey columns 5 µg/ml and black columns 10 µg/ml. The average values and standard error of the mean fluorescent intensity (MFI) are shown for three independent experiments performed in triplicate. Asterisks indicate significance accordingly: **, p<0.01.

FIG. 15A-B. Screening assay for the identification of inhibitors (binding antagonists) of the factor H H384 variant. The interaction of biotinylated 4IS heparin with immobilised FHCCP6-8(H384) and FHCCP6-8(Y384) recombinant proteins (closed circles and squares respectively) in the presence of varying concentrations of unmodified 4IS heparin (0-4000 µmol/well). In (A) the absolute level of binding activity is shown (after 20-min development time), demonstrating that there is more binding of the H384 allotype compared to the Y384 variant to 4IS heparin, while in (B) these data are shown as the percentage of binding seen in the absence of competitor. For both the H384 and Y384 proteins a similar amount of unmodified 4IS (approximately 20 µmol/well) competed out half the binding signal observed for biotinylated 4IS alone, where values are plotted as a mean absorbance (n=4)±S.E. Thus, this assay system is suitable for the screening of molecules that can compete for heparin binding to factor H and could be used to identify compounds that can differentially inhibit the H384 vs. the Y384 variant.

DETAILED DESCRIPTION OF THE INVENTION

In a preferred embodiment of the invention the target is a heparin molecule. For screening in accordance with this embodiment of the invention, rather than the use of the whole Factor H variants, as indicated above, conveniently recombinant proteins may be employed which provide a portion of the mature Factor H protein comprising the heparin binding site and amino acid residue 384 of CCP7 such that heparin-binding via the CCP7 module is retained. Such recombinant proteins may also be used in methods of the invention employing the alternative targets mentioned above.

When the target is heparin, binding may, for example, be determined by conventional heparin affinity chromatography, e.g. using a HiTrap heparin column (Amersham Biosciences), or heparin immobilised on an allylamine-coated plate (Mahoney et al. (2004) Anal. Biochem. 330, 123-129; allylamine-coated BD Heparin-binding plates (formerly EpranEx plates) as supplied by BD Biosciences, Sheffield, UK), or the interaction of biotinylated-heparin to immobilized proteins may be employed.

Preferably, the protein variants presented to the target may be recombinant proteins comprising a target binding fragment derived from the CCP6-8 portion of the H384 and Y384 variants of Factor H. A cDNA corresponding to CCPs 6-8 can be amplified from a clone encoding the H384 variant (Ripoche et al. (1988) Biochem J. 249, 593-602) and inserted into an expression vector for expression in E. coli to provide FHCCP6-8(H384) as described in the examples.

The sequence of FHCCP6-8(H384) is given in FIG. 7 and Table 2 below (SEQ ID NO: 1). Table 2 also gives the corresponding cDNA sequence (SEQ ID NO: 2). Site-directed mutagenesis may be used to obtain the corresponding Y384 variant, FHCCP6-8(Y384) (see in Table 3 below SEQ ID NO: 3, and the corresponding cDNA, SEQ ID NO: 4).

When recombinant proteins thus obtained were compared for heparin-binding ability by affinity chromatography on a HiTrap Heparin column, the H384 variant was found to elute at lower salt strength then the Y384 variant. This was opposite to the relative heparin binding abilities of the same allotypic variants observed using a well-characterised unfractionated heparin, the 4IS (Thomas et al. (1984) Thromb. Haemost. 52, 148-152; Mulloy et al. (2000) Thromb. Haemost. 84, 1052-1056), whether employing an affinity column or plate assay with immobilized heparin or immobilized protein variants (see Example 1). It is heparin giving such relative binding characteristics which is desired for use in identifying antagonists which preferentially inhibit binding of H384 Factor H compared with the Y384 variant of Factor H in accordance with the invention. Thus a preferred binding target is an unfractionated international standard heparin, especially, for example, the 4th or 5th international standard, although fractionated heparin of defined oligomer length may also be employed, e.g. heparin oligosaccharides ranging form 4- to 18-mers.

In one embodiment the method of the invention may be a screening assay in the form of affinity chromatography wherein the target is immobilised on the column. The H384 and/or Y384 variant of Factor H may then be applied on to the column. The ability of the test agent to wash the Factor H variant off the column may then be assessed. Alternatively the H384 and/or Y384 variant of Factor H may be immobilised on the column. The target may then be applied on to the column and the ability of the test agent to wash the target off the column may then be assessed.

In a preferred embodiment the method comprises a competition assay wherein the target is coated on a plate and the plate is then exposed to labelled H384 and/or labelled Y384 variant of Factor H. The ability of a test agent to wash the label off may then be assessed according to conventional assay means. For instance it may be preferred to use heparin bound to allylamine-coated plates; apply labelled recombinant proteins (e.g. biotinylated proteins); and then assay the ability of a test agent to displace label from the plates.

In another preferred embodiment of the invention the method comprises a competition assay wherein the H384 and/or Y384 variant of Factor H is coated on a plate and the plate is then exposed to labelled target. The ability of a test agent to wash the label off may then be assessed according to conventional assay means. For instance the Factor H variants may be immobilized on plates and incubated with labelled heparin, e.g. biotinylated heparin such as biotinylated 4IS or 5IS heparin, in the presence and absence of the test agent.

Labelling of the Factor H variant or the targets for use according to the abovementioned embodiments may take a number of different forms. In a preferred embodiment the label may be biotin and conventional assays used to detect biotinylation. Alternatively the labelling may be via direct binding of a labelled antibody to the variant or target. Alternatively the labelling may utilise two antibodies in a conventional "secondary" antibody assay (e.g. use of anti-Factor H antibody and secondary antibody labelling). It will be further appreciated that the label could be a radiolabel (e.g. the use of 35S-labelled heparin as a target). Furthermore, in preferred embodiments, the label may be a fluorescent label or a label capable of some colormetric detection. Alternatively the label may be a detectable product of an enzyme (e.g. horseradish peroxidase or a similar enzyme may be utilised).

According to one preferred embodiment of the invention the H384 and the Y384 variant of Factor H may be labelled with different fluorophores that may be detected at distinct wavelengths. The H384 variant may be labelled using the NHS Alexa Fluor 488 fluorophore creating a stable dye-protein conjugate via reaction with the primary amines of the protein. The NHS Alexa Fluor 488 fluorophore has absorption and fluorescence emission maxima of approximately 484 nm and 519 nm, respectively. The Y384 variant may be labelled using the same method but utilising NHS Alexa Fluor 555 that has different absorption and fluorescence emission maxima (approximately 555 and 565, respectively). The labelling of the proteins with fluorophores (or other labels) may be carried out in the presence of heparin (e.g. a well characterized heparin such as the 4th international standard or a heparin oligosaccharide of defined length) to prevent modifications of residues that may affect the activity of the protein. This allows an assay to be performed whereby displacement of the label from the target may be performed in a single reaction vessel (e.g the well of a microtitre plate) such that it will be possible to discriminate between agents that differentially displace the H384 and/or the Y384 variant from the target. It will be appreciated that assays utilising a single label (or two which are indistinguishable) will require parallel assays to be performed. For instance the method of the invention may require assays to be performed in two reaction vessels (e.g. adjacent wells in a microtitre plate) such that the effects of the test agent may be assayed on H384 and Y384 variant binding as two separate assays.

Preferred embodiments of the invention are based on plate assay systems, which may conveniently employ microtitre plates, the target may be heparin or this heparin may be substituted by heparan sulphate or dermatan sulphate which exhibits the desired differential binding of the protein variants. Example 2 illustrates identification of a suitable form of heparan sulphate, bovine kidney heparan sulphate.

As indicated above, binding targets of interest also include C-reactive protein (CRP) or a portion thereof which binds CCPs6-8 of Factor H and fibromodulin (FMOD), either glycosylated or lacking some or all glycosylation, or a portion thereof which binds CCPs6-8 of Factor H. For example, FMOD may be employed which has been treated with a glycosidase, e.g., with N-glycosidase F, to remove keratan sulphate. FMOD thus treated binds Factor H significantly better than the keratan sulphate-containing form and retains better binding ability for the Y384 variant of Factor H than the H384 variant of Factor H (see Example 4).

Whether employing heparin, heparan sulphate, dermatan sulphate, CRP or FMOD, in general it may be found particularly convenient to employ a plate assay format with either the binding target immobilized on the plate and the variant proteins labelled as discussed above, or the variant proteins immobilized on the plate and the binding target labelled. It may be preferred to use biotinylated target or biotinylated protein variants in which case detection may employ a labelled specific binding partner for biotin, e.g. enzyme-labelled avidin or streptavidin.

Where the target chosen is DNA, e.g. linearized plasmid DNA, then the DNA may be incubated with each protein variant in a fluid phase and formation of protein/DNA complex assessed by agarose gel electrophoresis (see Example 5). As indicated above, where necrotic cells are provided as the binding target for the protein variants, e.g. Jurkat T cells rendered necrotic as described in Example 6, then binding of the protein variants may be determined by using flow cytometry.

In a preferred embodiment of the invention the H384 variant and the Y384 variant of Factor H (for example the FHCCP6-8(H384) and FHCCP6-8(Y384) constructs) may be immobilised individually on the wells of a microtitre plate (preferably at a concentration between 0.01-10 µg/well). The immobilisation may be carried out in a suitable buffer with a pH in the range of 5.0-9.0 (e.g. 5-250 mM acetate, MES or HEPES buffer containing 0-250 mM NaCl, but preferably PBS). Alternatively the protein may be immobilised using sodium carbonate (e.g. at 20 mM, pH 9.6). Proteins would be incubated with the mictrotitre plate surface for between 0.5-24 hours at a temperature between 4° C. and 40° C. (e.g. 12-16 hours at room temperature). Control wells are incubated with buffer alone. Unbound protein is then removed by washing in a suitable buffer (e.g. 5-250 mM acetate, MES or HEPES buffer containing 0-250 mM sodium chloride with a pH of between 5.0-9.0 containing a detergent, e.g. 0.01-1% Tween 20). Washes are also carried out between all subsequent stages of the assay. Non-specific binding sites on the well surface may be blocked by incubation with a 0.1-10% albumin (preferably bovine serum albumin) or skimmed milk solution in a suitable buffer (e.g. 5-250 mM acetate, MES or HEPES buffer containing 0-250 mM sodium chloride with a pH of between 5.0-9.0 or PBS) for between 0.5-24 hours at 4-40° C. (e.g. 1% BSA for 90 min at 37° C.). The labelled target (typically 0.001-1000 pmol/well) is then incubated in the microtitre wells in the absence or presence of a test agent (e.g. 0.01-10,000-fold molar excess over the concentration of the target molecule). This incubation may be carried out in a suitable buffer (e.g. 5-250 mM acetate, MES or HEPES buffer containing 0-250 mM sodium chloride with a pH of between 5.0-9.0 containing a detergent, e.g. 0.01-1% Tween 20) at 4-40° C. for 0.5-24 hours (e.g. 4 hours at room temperature). The amount of labelled target bound to the well surface may then be determined using a suitable detection system. For example a biotinylated target would be detected by incubation with a solution of streptavidin conjugated with an enzyme such as alkaline phosphatase or horseradish peroxidase and the subsequent addition of a suitable substrate. Signals obtained from the control wells may be subtracted from those from the test wells to correct for any non-specific binding.

A most preferred method according to the invention is described in Example 7. This method is particularly suitable for identifying agents that differentially inhibit the binding of FHCCP6-8(H384) to heparin compared to FHCCP6-8 (Y384).

The following examples illustrate the invention with reference to the following figures.

Example 1

Binding of H384 and Y384 Variants of Whole Factor H and CCPs 6-8 to Heparin Experimental Procedures Purification of Full-Length Factor H from Human Serum Factor H was purified from 400 ml plasminogen/plasmin-depleted pooled human plasma (HD Supplies, High Wycombe, UK) (Sim et al. (1993) Methods Enzymol. 223, 13-35) on a 25-ml column of Sepharose to which was coupled a mouse anti-human Factor H mAb (MRC OX23) (Sim et al. (1983) Biosci. Rep 3, 1119-1131).

Heparin-Binding Site Predictions

Previously, coordinates for four models of intact Factor H were created from X-ray and neutron scattering data for purified Factor H along with homology modeling for 17 of the 20 CCPs based on known NMR structures for Factor H (CCP5, CCP15, CCP16) and vaccinia coat protein CCP3 and CCP4 (Aslam and Perkins 92001) J. Mol. Biol. 309, 1117-1138). We used three of these models (termed B, C and D; PDB accession code, 1haq) to predict heparin-binding sites on Factor H in conjunction with a heparin pentasaccharide model of heparin (Mulloy and Forster (2000) Glycobiology 10, 1147-1156)) using the program AutoDock, essentially as described before (Mahoney et al. (2005) J. Biol. Chem. 280, 2704-27055). All possible pairs of CCPs (e.g. CCP1-2, CCP2-3 etc.) were extracted from each model and XPLOR version 3.8 was used to add hydrogen atoms, build in the disulfide bonds and energy minimize the structures; three rounds of energy minimization were conducted, the first using a repulsive energy term only, the second also including a Lennard-Jones potential and the third with added electrostatics. Autogrid version 3 was used to create the docking grid with a box size of 120×120×120 points spaced at 0.7 Å intervals, a dielectric constant of 1.0, where the grid-centre was positioned at the centre of the CCP pair. Autodock version 2.4 was used for docking predictions using a simulated annealing protocol with 300 steps, where 128 runs were performed for each CCP pair with a heparin pentasaccharide model created previously (Mulloy and Forster ibid. In addition an Autodock prediction was performed for the CCP6-8 following the procedures described above.

Expression and Refolding of FHCCP6-8

Factor H cDNA corresponding to CCPs 6 to 8 (FHCCP6-8) was amplified from Factor H clone PE3 (Ripoche et al. (1988) Biochem. J. 249, 593-602) which encodes the H384 variant, and was modified by PCR to include NcoI and BamHI restriction sites allowing ligation into a pET14b vector (Merck, Nottingham, UK); primers, which are shown in Table 1, were synthesised by Applied Biosystems (Warrington, UK). Analysis of the construct on an ABI 3730×1 Prism DNA sequencer using T7 promoter and terminator primers determined that there were no changes to the expected sequence. As shown in FIG. 7, the expressed protein sequence (SEQ ID NO: 1) starts with a non-authentic glycine at the beginning of the FHCCP6-8 (H384) sequence resulting from engineering of the NcoI restriction site; the initiating methionine is removed during expression. The corresponding DNA construct was transformed into BL21(DE3)pLysS competent cells (Merck) using the manufacturer's protocol, expressed in E. coli and refolded using a method described previously for CCP modules (White et al. (2004) Protein Sci. 9, 2406-2415). The protein was purified to homogeneity using anion exchange on a 1-ml Mono Q column (Amersham Biosciences, Buckinghamshire, UK) equilibrated in 20 mM 3-(cyclohexylamino)-1-propanesulphonic acid (CAPS), 130 mM NaCl, 1 mM EDTA, pH 10.0 and eluted with a gradient of 130 mM to 1M NaCl over 20 min. The collected fractions were analyzed by SDS-PAGE and the protein was found to be >98% pure where the protein under reducing conditions had a lower mobility than the non-reduced material. One-dimensional NMR spectroscopy at 600 MHz (pH 7.3) indicated that the protein was folded (e.g., up-field shifted methyl resonances were observed) and the presence of disulfide bonds was determined by analysis of trypsin digests by MALDI-TOF mass spectrometry. Protein concentrations were determined by amino acid analysis.

TABLE 1

Primers for PCR and site-directed mutagenesis
Text in bold highlights the codon of interest and
the underlined text are the bases that have been
changed to give the desired residue change and are
shown in the 5'-3' orientation.

| Primer name[a] | Sequence (5'-3') | Tm | %GC |
|---|---|---|---|
| FHCCP6-8 construct primers[b] | | | |
| FHCCP6-8 S | AATTAAAT *CCATGG* GTACCTTGAAACCTTGTGATTATCC (SEQ ID NO: 5) | 64 | 39 |
| FHCCP6-8 AS | AA *GGATCC* TTAAATGCACGTGGGTTGAGCTG (SEQ ID NO: 6) | 62 | 55 |
| Mutational primers[c] | | | |
| H384Y S | GATATAATCAAAATTATGAAGAAAGTTTGTACAGG (SEQ ID NO: 7) | 72 | 31 |
| H384Y AS | CCTATATTAGTTTTA GTA CCTTCTTTCAAACATGTCC (SEQ ID NO: 8) | | |
| K370A S | CAGCAGTACCATGCCTCAGA GCA TGTTATTTTCCTTATTTG (SEQ ID NO: 9) | 75 | 38 |
| K370A AS | GTCGTCATGGTACGGAGTCT CGT ACAATAAAAGGAATAAAC (SEQ ID NO: 10) | | |
| R386A S | GGATATAATCAAAATCATGGA GCA AAGTTTGTACAGGGTAAATC (SEQ ID NO: 11) | 73 | 31 |
| R386A AS | CCTATATTAGTTTTAGTACCT CGT TTCAAACATGTCCCATTTAG (SEQ ID NO: 12) | | |

TABLE 1-continued

Primers for PCR and site-directed mutagenesis
Text in bold highlights the codon of interest and
the underlined text are the bases that have been
changed to give the desired residue change and are
shown in the 5'-3' orientation.

| Primer name[a] | Sequence (5'-3') | Tm | %GC |
|---|---|---|---|
| K387A S | GATATAATCAAAATCATGGAAGA GCG TTGTACAGGGTAAATCTATAG (SEQ ID NO: 13) | 75 | 30 |
| K387A AS | CTATATTAGTTTTAGTACCTTCT CGC AAACATGTCCCATTTAGATATC (SEQ ID NO: 14) | | |

[a]S = sense, AS = anti-sense;
[b]Restriction sites for NcoI and BamHI are in bold italics;
[c]Mutated nucleotides are underlined with altered codon shown in bold.

Site-Directed Mutagenesis

Mutagenesis was carried out using PCR with the QuikChange Site-Directed Mutagenesis Kit (Stratagene, Amsterdam, The Netherlands), as recommended in the manufacturer's manual but using 18 amplification cycles in the reaction; primers (Applied Biosystems) are defined in table S1. Residues K370, R386 and K387 were individually mutated to alanine in the context of the FHCCP6-8(H384) construct and confirmed by DNA sequence analysis as above. In addition H384 was altered to tyrosine. The proteins were expressed, purified and characterized by 1-D NMR spectroscopy and disulfide mapping as described above.

Heparin and Protein Biotinylation

For the biotinylation of unfractionated heparin (the 4th International Standard (4IS)), 13 µl of a 25 mg/ml solution of 1-ethyl-3-(3-dimethylaminopropyl)carbo-dimide hydrochloride (EDAC) (Sigma, Poole, UK) in 0.1 M MES, pH 6.5 was added to 7.91 mg 4IS heparin in 1 ml 0.1 M MES buffer, pH 6.5. Then 20 µl of 50 mM biotin-LC-hydrazide (Pierce, Northumberland, UK) in dimethylsulphoxide (freshly made) was added to the heparin/EDAC reaction and left to mix by rotation at room temperature overnight. The reaction mixture was dialyzed using a 500-Mw cut off dialysis membrane (Pierce) against 10 L of water.

The histidine and tyrosine variants of FHCCP6-8 were biotinylated using a similar method. Briefly, 200 µg of protein in 462 µl of water was added to 124 µl 0.2 mg/ml EZlink N-hydroxysuccinimide-LC Biotin (Pierce) in 100 mM NaHCO₃, pH8.5 and rotated at room temperature for 1 hour. Excess biotin was removed from the reaction mixture using a 250×10-mm C5 HPLC column (Phenomenex, Macclesfield, UK), equilibrated in 0.1% (v/v) trifluoroacetic acid (TFA), and the biotinylated protein was eluted with an 10-80% acetonitrile gradient over 35 min and collected manually. The protein was recovered on a centrifugal evaporator (Savant, Minn., USA) and reconstituted in PBS (137 mM NaCl, 2.6 mM KCl, 8.2 mM Na₂HPO₄, 1.5 mM KH₂PO₄, pH 7.3; Oxoid (Basingstoke, UK)).

Heparin Affinity Chromatograhy

The heparin-binding properties of H384 and Y384 variants of FHCCP6-8 were compared to full-length human factor H by affinity chromatography on a HiTrap Heparin column (Amersham Biosciences) or a 'home-made' column in which 20 mg 4IS was coupled to 1.5-ml CNBr-activated Sepharose (Sigma) in 0.1 M NaHCO₃, 0.5 M NaCl, pH 8.3 using the manufacturer's protocol. The 1-ml HiTrap column and ~1-ml 4IS-column were equilibrated in 20 mM HEPES, 130 mM NaCl, 1 mM EDTA, pH 7.3. Protein (200 µg recombinant proteins; 100 µg full-length factor H) was loaded onto the columns (in 1 ml equilibration buffer) and any unbound material was removed with 5 column volumes of the same buffer and collected in 1-ml fractions. Protein was eluted from the columns using a linear salt gradient of 130 mM to 1 M NaCl over 20 min by mixing 20 mM HEPES, 1 M NaCl, 1 mM EDTA, pH 7.3 with the equilibration buffer at a flow rate of 1 ml/min. One ml fractions were collected and analyzed by SDS-PAGE, which demonstrated that the species eluting between 340-460 or 170-290 mM NaCl, for the HiTrap and 4IS columns, respectively, corresponded to FHCCP6-8/factor H proteins.

This approach was also used to determine the relative heparin-binding activities of K370A, R386A and K387A mutants, where 200 µg of protein was loaded individually onto the HiTrap column.

Microtitre Plate Assays

The heparin/HS/DS-binding activities of the FHCCP6-8 (H384) and FHCCP6-8(Y384) variants (using biotinylated-FHCCP6-8 constructs), and in some cases full-length Factor H (detected with an antibody), were compared using an assay where the glycosaminoglycans (GAGs) were immobilized on allylamine-coated EpranEx plates (Mahoney et al (2004) Anal. Biochem. 330, 123-129), kindly supplied by Plasso Technology Ltd., Sheffield, UK. Previously, we have shown that heparin/HS can bind non-covalently to surfaces plasma polymerized with allylamine in such a way that these GAGs can still associate with a wide-range of proteins (Mahoney et al. (2005) J. Biol. Chem. 280, 27044-27055; Mahoney et al. (2004) ibid).

The following GAG preparations were analyzed: unfractionated heparins corresponding to the 2nd, 4th and 5th International Standards (denoted here as 2IS, 4IS and 5IS, respectively (Mulloy et al. (2000) Thromb. Haemost. 52, 148-153)); enoxaparin, dalteparin and LMr heparin from Sigma (Cat. No. H3400); selectively desulfated heparins prepared from 2IS heparin as described in Mulloy et al. (1994) Carbohydr. Res. 255, 1-26 and Ostrovsky et al. (2002) J. Biol. Chem. 277, 2444-2453; HSI and HSII preparations of heparan sulphate (HS) (Mahoney et al. (2005) ibid); biotinylated bovine kidney heparan sulphate (Sigma) and dermatan sulphate (DS) purified from porcine mucosa and characterized by NMR as described previously (Pavão et al. (1995) J. Biol. Chem. 270, 31027-31036) on a Varian Inova 500 MHz spectrometer at 60° C. in D₂O. The GAGs (200 µl/well; 1 µg) were coated overnight at room temperature onto EpranEx plates in PBS. Plates were blocked with 1% (w/v) BSA (Sigma, Cat. No. A-4503) in standard assay buffer (20 mM HEPES, 130 mM NaCl, 0.05% (v/v) Tween-20, pH 7.3) for 90 minutes at 37° C. The standard assay buffer was used for all subsequent incubations, dilutions and washes at room temperature. The proteins were incubated at various concentrations with the immobilized glycosaminoglycans for 4 hours.

In the case of the biotinylated FHCCP6-8(H384) and FHCCP6-8(Y384) constructs, bound material was detected by adding 200 µl/well of a 1:10,000 dilution of ExtrAvidin alkaline phosphatase (Sigma, Cat. No. E-2636) for 30 minutes. Plates were then developed with 200 µl/well of 1 mg/ml disodium p-nitrophenylphosphate (Sigma) in 0.05 M Tris-HCl, 0.1 M NaCl, pH 9.3, and developed for 40 minutes, except for the DS-coated plates that were developed for 50 min. For the full-length protein, the level of binding (to 4IS, HSI and HSII) was determined by incubation of the plates for 30 min with MRC OX23 (a monoclonal antibody against factor H (Sim et al. (1983) Biosci. Rep. 3, 1119-1131; 1 µg/well) followed by a 1:1000 dilution of alkaline phosphatase-conjugated goat anti-mouse IgG (Sigma, Cat. No. A-3438) for another 30 minutes. The plates were then developed for 10 min as described above. The absorbance values at 405 nm were determined and corrected against blank wells (i.e., those that contained no GAGs).

Alternatively, the unlabelled FHCCP6-8(H384), FHCCP6-8(Y384) and mutant proteins (i.e., K370A, R386A, K387A in the context of the FHCCP6-8(H384) construct) were adsorbed at 1 µg/ml in PBS onto microtitre plates (Nunc Maxisorb, Kastrup, Denmark) and their ligand-binding activities at pH 7.3 were determined using biotinylated-4IS heparin essentially as described in Mahoney et al. (2005) ibid. Plate assays were carried out in 20 mM HEPES, 130 mM NaCl, 0.05% (v/v) Tween-20, pH 7.3 and the level of bound heparin determined as described above for the biotinylated proteins.

In these plate assays all data points were determined in quadruplicate from each of two independent experiments.

Results and Discussion

Heparin-Binding Sites on Factor H

Our analysis indicated that two CCP modules of Factor H (7 and 20) harbor interaction sites for heparin, consistent with previous biochemical studies (Blackmore et al. (1996) J. Immunol. 157, 5422-5427; Blackmore et al. (1998) J. Immunol. 160, 3342-3348; Herbert et al. (2006) J. Biol. Chem.). In CCP7 docking calculations consistently placed the bound pentasccharide model in close proximity to three basic amino acids (K370, R386, K387), the latter two of which are adjacent to residue 384 (see FIG. 1).

Heparin-Binding Residues in CCP7

Recombinant FHCCP6-8(H384) was demonstrated to be correctly folded, having the expected disulfide bond arrangement, and to bind to heparin in a variety of assays (FIG. 2), providing evidence that this region of Factor H is involved in the recognition of polyanions. Mutants were produced in the context of this construct so that K370, R386, K387 were individually altered to alanine. One-dimensional NMR spectroscopy demonstrated that the mutants all had essentially identical spectra to the wild-type protein, indicating that these alterations do not perturb the tertiary structure of the protein. Furthermore, these proteins all had identical disulphide bond patterns. The effect of mutation on heparin-binding function was assessed using affinity chromatography, or using a microtitre plate assay, where the proteins were immobilized and the binding of biotinylated heparin was determined. As can be seen from the chromatograph in FIG. 3A, the R386A and K387A mutants have substantially reduced binding activity compared to wild-type FHCCP6-8(H384), eluting from the heparin affinity column at lower NaCl concentrations, whereas mutation of K370 to alanine had no affect. Results from the plate assay were consistent with this (FIG. 3B). However, the K370A protein showed a small reduction in binding. These data indicate that R386 and K387 are both likely to play an important role in heparin binding. This is consistent with an earlier study where these amino acids were replaced with alanine in a double mutant expressed in the context of CCP1-7 which was shown to have reduced binding to heparin-BSA (Giannakis et al. (2003) Eur. J. Immunol. 33, 962-969); in this case no structural studies were undertaken to assess the effect of mutagenesis on the protein fold. Furthermore, Giannakis and colleagues reported that a R369A/K370A double mutant had greatly reduced heparin-binding function. Our data indicate that K370 has a minor contribution, if any, to the association with heparin. However, a proportion of the K370A protein eluted at a lower salt strength, indicating that this residue may be involved in the binding to a sub-fraction of heparin structures on the column.

Determining the Role of H384/Y384 in Heparin Binding

Given that H384 is in close proximity to the heparin-binding residues on CCP7 (see FIG. 1) it seemed plausible that this amino acid may participate in the interaction with heparin and that the histidine and tyrosine variants could have different functional activities. Therefore, FHCCP6-8(H384) was mutated to tyrosine to generate the FHCCP6-8(Y384) protein and their heparin-binding properties compared; FHCCP6-8(Y384) was shown to be folded, with correct disulfides, as before. From FIG. 2A, it is apparent that the H384 variant elutes at lower salt strength than Y384 from the HiTrap heparin affinity column (340 and 390 mM NaCl, respectively), whereas a higher salt strength is required to recover intact Factor H. It is not surprising that the full-length protein binds more tightly to the affinity column given that it has at least two sites of heparin binding (i.e., CCP7 and CCP20). However, the finding that it can be eluted at 460 mM NaCl, which is not substantially higher than for the FHCCP6-8(Y384) protein, suggests that the heparin-interaction site in CCP7 makes a major contribution to this activity.

The relative heparin-binding activities of the allotypic variants were further analyzed by microtitre plate assays. Either the proteins were immobilized and their interaction with biotinylated-heparin determined (FIG. 2B), or heparin was bound to an allylamine-coated surface and used to assess the binding of the Y384/H384 proteins, where these had been biotinylated (FIG. 2D). For these experiments, a well-characterized unfractionated heparin (4IS) was utilized. In both cases FHCCP6-8(Y384) was shown to bind less well to the 4IS heparin than the FHCCP6-8(H384) variant. This is the inverse of the result using affinity chromatography (FIG. 2A), which was performed on a commercial HiTrap heparin column where the exact source and composition of heparin has not been made known. Therefore, to rule out that this was an artifact resulting from the different assays used, we analyzed the binding of these proteins to a column to which 4IS heparin had been coupled. As can be seen from FIG. 2C, the relative binding affinities of FHCCP6-8(Y384) and FHCCP6-8(H384) are consistent with the plate assay data, where an identical source of heparin was employed. It seems possible therefore, that not only do the H384/Y384 allotypic variants have distinct heparin-binding activities but that they can also differentiate between heparins of different structure.

Characterization of the H384/Y384 Variant-Heparin Interaction

Figure 8:
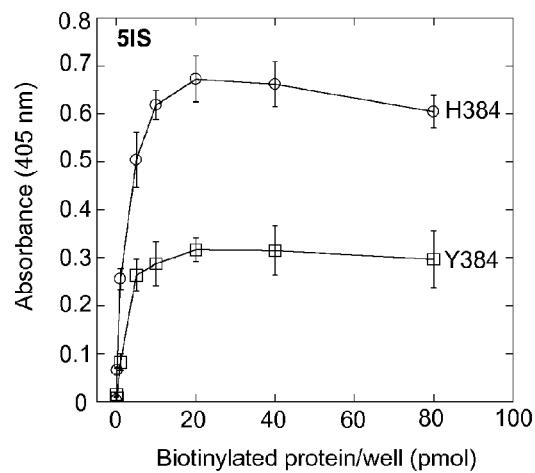
Figure 8:
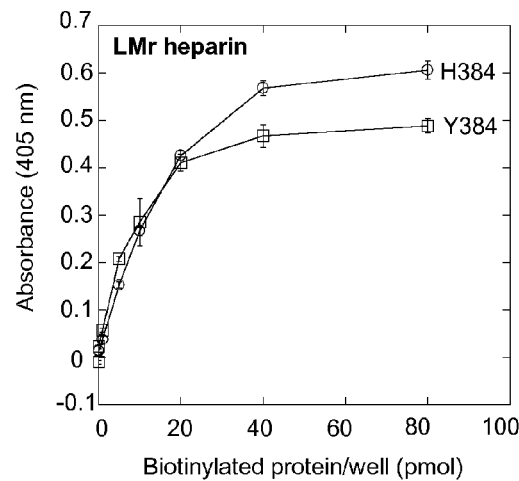
Figure 8:
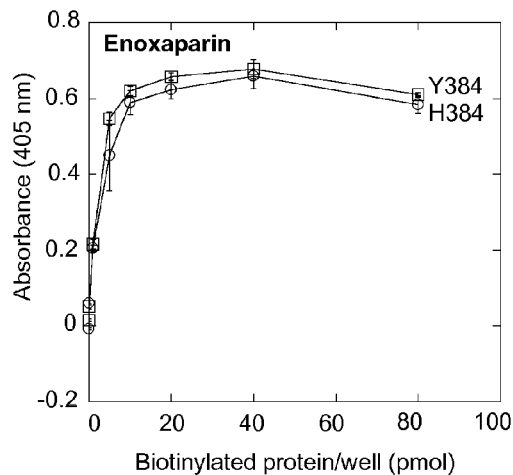
Figure 8:
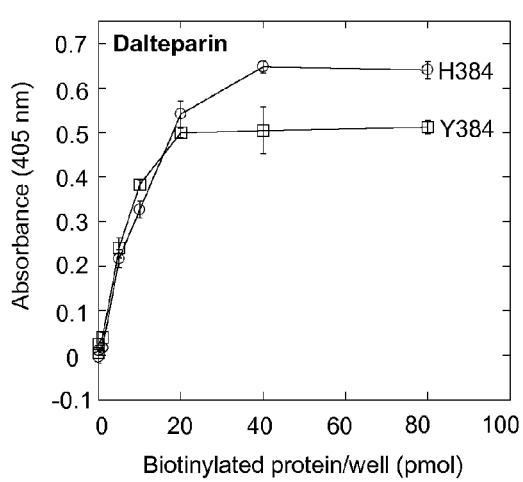

In order to investigate this further, we analyzed the binding of the FHCCP6-8(Y384) and FHCCP6-8(H384) proteins to a wide range of heparin preparations. For the three unfractionated heparins tested (i.e., 2IS, 4IS and 5IS), more of the FHCCP6-8(H384) protein bound to the immobilized glycosaminoglycans compared to the FHCCP6-8(Y384), the 4IS and 5IS preparations giving essentially identical results (see FIG. 2D and FIG. 8A). The difference was less marked for the 2IS (FIG. 4A) due to an increased level of binding for the FHCCP6-8(Y384) protein. In the case of the low molecular weight heparins, there was no difference in the binding of the two constructs to enoxaparin (FIG. 8C), and only a small difference was observed for their binding to dalteparin (FIG. 8D) and the LMr heparin obtained from Sigma (FIG. 8B). These data indicate that the results obtained for FHCCP6-8 (H384) and FHCCP6-8(Y384), including their differential binding activities, are dependent on the type of heparin used and, thus, may correlate with differences in the structure/composition of these preparations. That said, it is difficult to attribute the differences in binding seen for the H384 and Y384 proteins to specific structural features. Therefore, in order to provide some insight into this we investigated the effect of selective desulphation of IS2 heparin on its binding to FHCCP6-8(H384) and FHCCP6-8(Y384).

Figure 4:
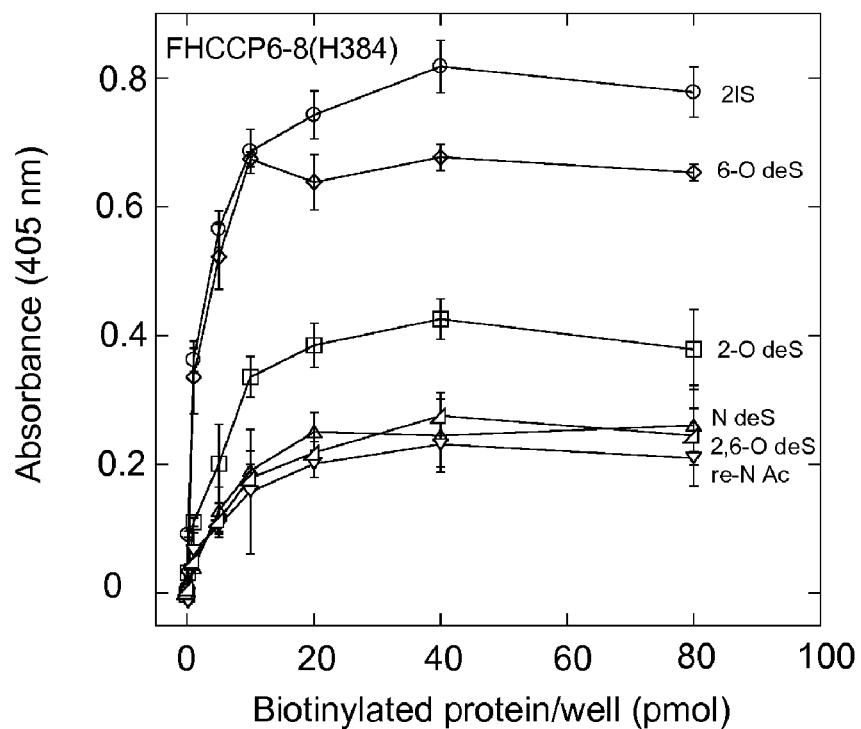
Figure 4:
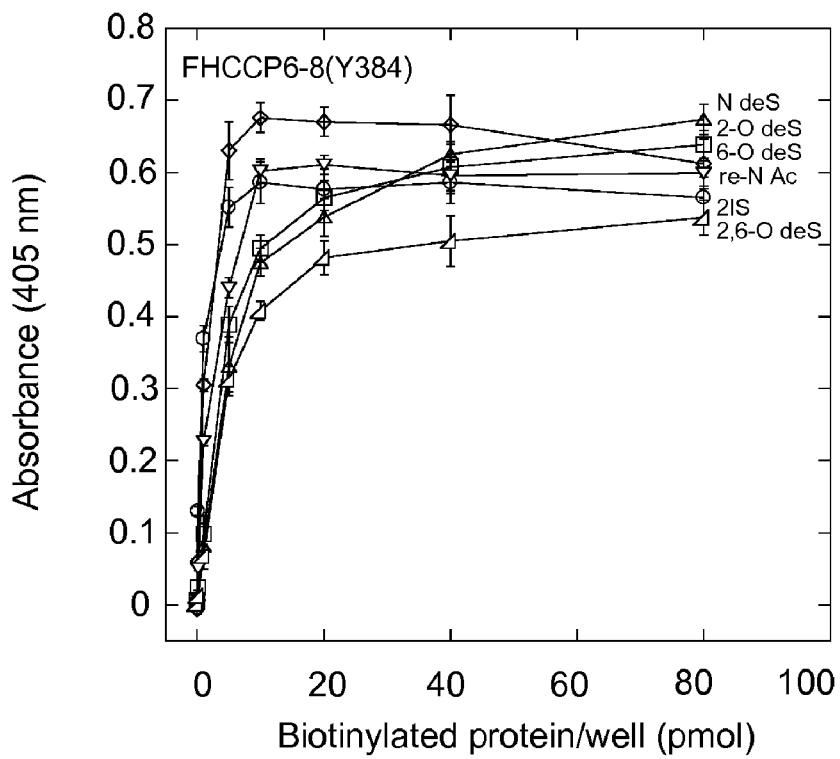

As can be seen from FIG. 4, the desulphation of heparin has a much larger effect on its interaction with the FHCCP6-8 (H384) protein compared to FHCCP6-8(Y384). In this regard, the removal of either the 2-O-(2-O-deS) or N-sulfate (N-deS) leads to a large reduction in the binding of the H384 variant (FIG. 4B,E), where re-N-acetylation of the N-deS preparation (N-deS/reN-Ac) has no additional/compensating effect (FIG. 4F). Interestingly, the binding of the Y384 variant appears to be less sensitive to loss of these functional groups, where its binding to the 6-O-deS and N-deS/re-N-Ac preparations appears to be indistinguishable from the parental 2IS material. Furthermore, removal of 2-O-, 2,6-O- or N-sulfates only has a small effect on the FHCCP6-8(Y384) interaction (as determined from a comparison of the shapes of the binding curves relative to unmodified 2IS). From the above experiments, it is apparent that the FHCCP6-8(Y384) protein can bind more strongly to particular heparin preparations than the FHCCP6-8(H384) form, consistent with the data from the HiTrap heparin affinity column (see FIG. 2A). However, in other cases (i.e., 2IS, 4IS and 5IS), it is the histidine form of the protein that exhibits greater binding activity. This analysis provides compelling evidence that the H384/Y384 allotypic variants of factor H recognize different structural features within heparin.

Comparison of the Interactions of FHCCP6-8(H384) and the Corresponding Y384 Variant with Heparin Oligomers of Different Lengths As shown in FIG. 10, the H384 and Y384 protein variants exhibited different properties when their binding to heparin oligosaccharides of defined length (ranging from 4- to 18-mers) was compared. In all instances, the H384 variant bound better. Interestingly, the interaction of FHCCP6-8 (Y384) to the immobilized oligomers appears to be length dependent (with maximal binding to oligosaccharides of ~12 sugars in length), whereas for FHCCP6-8(H384) this was not the case. Control experiments revealed that the binding of biotinylated-heparin to immobilized H384 and Y384 could be competed completely by dp4 oligomers, showing that these interactions are specific.

Example 2

Figure 5:
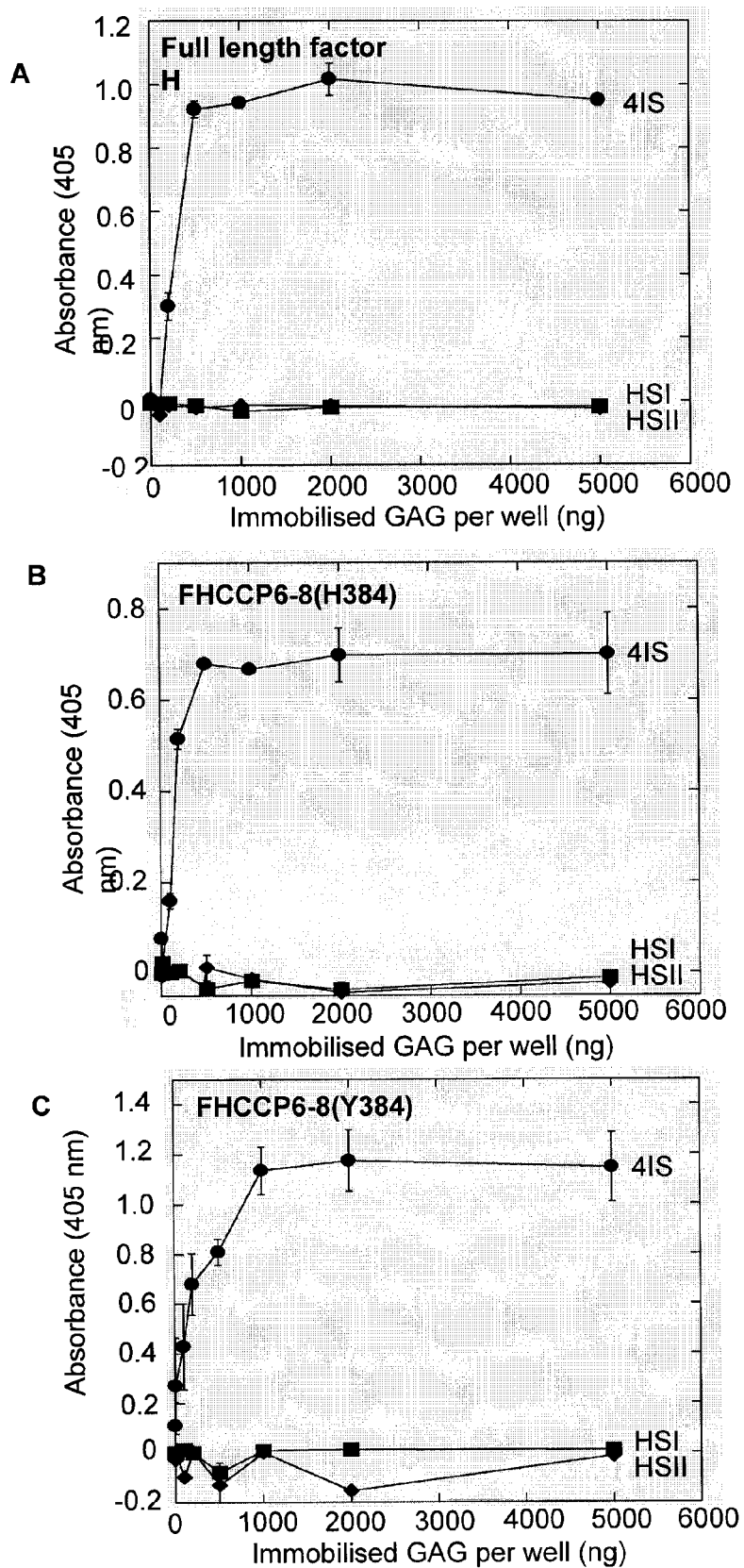

Heparan Sulphate (HS) Binding to Full Length FH and H384/Y384 Constructs Preliminary Studies with HS Preparations Unexpectedly, neither the FHCCP6-8(H384/Y384) constructs nor full-length Factor H bound to the HS preparations initially tested in the assay where the HS preparations were immobilized on an allylamine-coated EpranEx plate (FIG. 5); HSI and HSII have different levels of sulphation, where the latter is more highly sulphated than the former (see Mahoney et al (2005) ibid). This lack of activity may be a consequence of the assay used, however, we have previously seen binding of another protein (TSG-6) to HSI and HSII preparations immobilized on EpranEx plates.

Factor H interaction with HS would seem likely to be through its recognition of a distinct structural feature (e.g., sulphation pattern), which is clearly present within heparin (e.g., 3-O-sulphation, which is an essential component of anti-coagulant heparin sulphate), rather than being dependent on the absolute level of sulphation.

Biotinylated Bovine HS Plate Assay

The HS binding properties of FHCCP6-8(H384), FHCCP6-8(Y384) and full length Factor H were further tested using biotinylated bovine kidney heparan sulphate (Sigma) where the proteins were coated onto the wells of a Maxisorp microtitre plate (NUNC) at 1 µg/well in PBS (Oxoid; 137 mM NaCl, 2.6 mM KCl, 8.2 mM $Na_2HPO_4$, 1.5 mM $KH_2PO_4$, pH 7.3) overnight at room temperature. Link_TSG6 (denoted as L-TSG-6 in FIG. 9), a known HS-binding domain (see Mahoney et al. (2005) J. Biol. Chem. 280, 27044-27055) was immobilised at 1 µg/well as a positive control. Plates were blocked the next morning with 1% (w/v) BSA (Sigma, Cat. No. A-4503) in standard assay buffer (20 mM HEPES, 130 mM NaCl, 0.05% (v/v) Tween-20, pH 7.3) for 90 minutes at 37° C. The standard assay buffer was used for all subsequent incubations, dilutions and washes at room temperature. The biotinylated HS was incubated at various concentrations with the immobilised proteins for 4 hours. Bound material was detected by adding 200 µl/well of a 1:10,000 dilution of ExtrAvidin alkaline phosphatase (Sigma, Cat. No. E-2636) for 30 minutes. Plates were then developed with 200 µl/well of 1 mg/ml disodium p-nitrophenylphosphate (pNPP; Sigma) in 0.05 M Tris-HCl, 0.1 M NaCl, pH9.3, and developed for 40 minutes; the absorbance at 405 nm was measured and the signal from blank wells subtracted.

Immobilised full length Factor H, FHCCP6-8(H384) and FHCCP6-8(Y384) were all found to interact with biotinylated bovine kidney HS. The Y384 and H384 constructs have somewhat different binding activities as shown in FIG. 9.

Example 3

Binding of FHCCP6-8(H384) and FHCCP6-8(Y384) to Dermatan Sulphate

The binding of the FHCCP6-8(H384) and FHCCP6-8 (Y384) proteins to DS was also investigated since Factor H has been previously reported to bind to this GAG (Saito and Munakata (2005) J. Biochem. 137, 225-233). From FIG. 6, it can be seen that these constructs do interact with DS, albeit to a lesser degree than heparin, and appear to have somewhat different binding properties. The DS used was of high purity, where the $^1$H NMR spectrum did not contain resonances attributable to heparin impurities; signals from the H1 of N-sulfate or N-acetylated glucosamine, which do not coincide with any resonances in the DS spectrum, were absent. Furthermore, almost all the intensity in the spectrum could be assigned to signals from the repeating unit [α-L-IdoA-(1-4)-β-D-GalNAc4SO$_3^-$(1-4)], containing a few percent of [α-L-IdoA2SO$_3^-$-(1-4)-β-D-GalNAc4SO$_3^-$(1-4)]. This makes it likely, therefore, that Factor H is a bone fide DS-binding protein and that the H384/Y384 allotypic forms may differentially recognize DS-containing proteoglycans in vivo.

Example 4

Binding of FHCCP6-8(H384) and FHCCP6-8(Y384) to CRP and FMOD

FMOD was isolated from bovine articular cartilage (Heinghrd et al., (1986) J. Biol. Chem. 261, 13866-13872) and recombinant CRP was obtained from Calbiochem. Deglycosylated FMOD was prepared by treatment with N-glycosiadase F (Roche Applied Science) as previously described (Sjöberg et al. (2005) J. Biol. Chem. 280, 32301-32308).

Protein/Protein Binding Assays

CRP or FMOD was coated overnight at 4° C. onto microtiter plates (Maxisorp, Nunc) at a concentration of 10 µg/ml in 75 mM sodium carbonate buffer, pH 9.6. Wells treated only with coating buffer or 1% (w/v) BSA (Sigma) in coating buffer (for the assays involving FMOD) were used as negative controls. Between each step the wells were washed extensively with 50 mM Tris-HCl, 150 mM NaCl, 0.1% (v/v) Tween 20, pH 7.5. All wells were blocked with 1% (w/v) BSA (Sigma) in phosphate buffered saline (Invitrogen) for 1 hour at 37° C. FHCCP6-8(H384) and FHCCP6-8(Y384) were added at varrying concentrations in the binding buffer (50 mM HEPES, 100 mM NaCl, 2 mM CaCl$_2$, pH 7.4); full length FH served as a positive control. In the experiments with FMOD, 50 µg/ml BSA was included in the binding buffer. The amount of bound protein was assessed using a goat polyclonal anti-FH antibody (Quidel, Cat # A312) followed by HRP-labeled anti-goat secondary antibodies (Dako) and the OPD development kit (Dako). Detection of biotinylated protein was performed using a StreptABComplex/HRP-kit from Dako, and in both cases the absorbance at 490 nm was measured to quantify protein binding.

Results

In the case of CRP, the Y384 variant bound significantly better than the H384 variant (p<0.03 for all data points above zero) and this was evident in a dose-dependent manner (FIG. 11A). To verify that our results reflected true differences in the interaction of CRP with FHCCP(H384) and FHCCP (Y384) and not differential recognition of the two allotypic variants by the polyclonal antibodies used for detection, we repeated the experiment with biotinylated proteins. Using a selected range of concentrations, we showed the same trend of lower CRP binding with the H384 variant (FIG. 11B). Thus, the disease-associated variant of FH has impaired ability to interact with CRP, which may lead to an increase of complement activation by CRP, perhaps to the point of development of chronic inflammation in the affected tissue. FH interacts with dying cells and this binding has been reported to be increased in the presence of CRP (Gershov et al. (2000) J. Exp. Med. 192, 1353-1363). Decrease in FH-CRP interaction could lead to lesser deposition of FH on dying cells, which in turn could result in excessive complement activation on such debris and further the development of inflammation in the macula.

Figure 12:
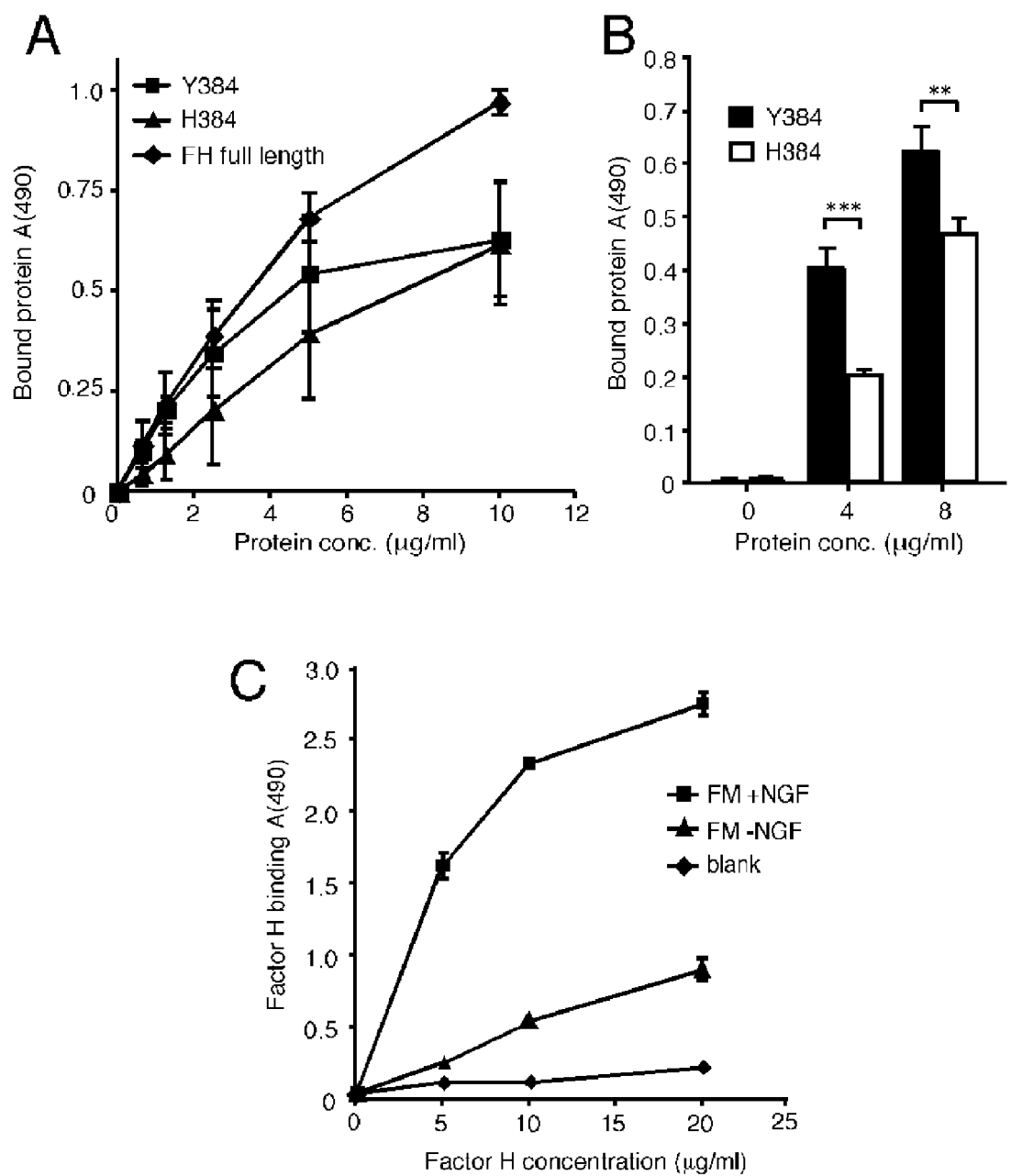

Using a direct binding assay as described above, we also showed that FMOD interacts directly with the CCP6-8 region of FH and that the affinity is increased in the Y384 variant compared to the H384 variant (FIG. 12). When detecting biotinylated FHCCP6-8 variants bound to immobilized FMOD, we detected significantly stronger signals for the Y384 variant at all concentrations tested (FIG. 12B). In the assay detecting unlabelled FHCCP6-8 variants with a specific polyclonal antibody, there is significant difference (p<0.02) for two concentration points and the binding curves meet at the highest concentration. Throughout the experimentation, we saw a clear trend towards stronger binding for the tyrosine 384 variant of FHCCP6-8. Although weaker, this trend is the same as that observed for the interaction between CRP and FHCCP6-8 variants. We speculate that these two separate binding events co-operate towards a more pro-inflammatory disease progression, since complement regulation on CRP and FMOD will be hampered in patients with the H384 allotype.

The glycosylation state of FMOD (e.g. keratan sulphate attachment) may modify its interactions with its ligands. For example, it is not known whether FH binds the polypeptide of FMOD or rather to its keratan sulphate chains. In order to address this question, we deglycosylated FMOD using N-glycosidase F, an amidase which removes N-linked oligosaccharides (including keratan sulphate). We found that the deglycosylated FMOD bound FH significantly better than the keratan sulphate-containing form (p<10-4 for all data points above zero) (FIG. 12C). It appears therefore that the binding site for FH on FMOD is localized to the polypeptide chain and that the keratan sulphate causes steric hindrance for the interaction. When evaluating the effect of deglycosylation on binding to the FHCCP6-8 variants the same result was observed.

Example 5

Binding of FHCCP6-8(H384) and FHCCP6-8(Y384) to DNA

Plasmid pcDNA3 DNA (Invitrogen) was linearized using EcoR1 (Fermentas) in a buffer accompanying the enzyme.

Protein/DNA Binding Assay

Linearized pcDNA3-vector (30 ng) was incubated with 5 µg of FHCCP(H384), FHCCP6-8(Y384) or full length FH (positive control) in the binding buffer (as described above) in a total volume of 20 µl for 30 minutes at 37° C. The negative control contained no protein. DNA loading buffer (0.25% (w/v) bromophenol blue, 0.25% (w/v) xylene cyanol, 30% (v/v) glycerol in deionized water) was added (1 µl) and the samples were run on an agarose gel (0.8% (w/v), Cambrex) containing ethidium bromide (Sigma) and visualized by UV. Changes in DNA migration served as a means of evaluating the presence of DNA-protein complexes.

Results

When comparing with full-length FH (positive control) and DNA only (negative control), we observed that both FHCCP variants bound DNA but to different degrees. The H384 variant retained DNA in its protein-complex form more efficiently than the Y384 variant (FIG. 13). In fact, DNA incubated with the Y384 variant migrated mainly in the non-complexed form. Furthermore, we observed DNA-protein complexes in the samples containing the FHCCP6-8 variants (particularly with H384) migrated towards the anode. This is probably due to formation of larger positively charged protein-DNA complexes. The FHCCP6-8 constructs have a pI of ~7.9, consistent with this, whereas full-length FH has a pI of <7.0.

Example 6

Cell Assays

Jurkat T cells (ATCC), were grown in RPMI, supplemented with glutamine, penicillin, streptomycin and 10% (v/v) heat inactivated FCS (all from Invitrogen). Necrosis was induced by heat whereby the cells were brought to a concentration of $10^6$ per ml and incubated at 56° C. for 30 minutes in RPMI 1640 without FCS (Trouw et al. (2005) J. Exp. Med. 201, 1937-1948).

Flow Cytometry

Binding of FHCCP6-8 variants to necrotic cells was analyzed using flow cytometry. Protein binding was analyzed by incubating cells with varying concentrations of the FHCCP6-8 variants (0 to 10 μg/ml) in FACS binding buffer (10 mM HEPES, 150 mM NaCl, 5 mM KCl, 1 mM $MgCl_2$, 1.8 mM $CaCl_2$), with shaking for 30 minutes at room temperature. After washing twice in the same buffer, cells were stained with goat anti-FH polyclonal antibodies (Quidel) for 30 minutes at room temperature. This was followed by matched FITC-labelled secondary antibodies (Dako).

Results

FIG. 14 shows that at low concentrations both protein variants bind necrotic cells equally well, but at the concentration of 10 μg/ml the H384 variant binds necrotic cells better than the Y384 variant.

It will be appreciated that any of the binding assays as described above in which the two recombinant FHCCP6-8 protein variants show differential binding to the target may be employed for screening for preferential inhibitors of binding of the H384 variant in accordance with the invention.

Example 7

A Preferred Screening Assay for Identifying Molecules that Differentially Inhibit the Binding of FHCCP6-8(H384) to Heparin Compared to FHCCP6-8(Y384)

The inventors developed an assay that represents a preferred method to be employed according to the invention.

Competition Assay

Unlabelled FHCCP6-8(H384) and FHCCP6-8(Y384) proteins were adsorbed at 1 μg/ml in PBS (137 mM NaCl, 2.6 mM KCl, 8.2 mM $Na_2HPO_4$, 1.5 mM $KH_2PO_4$, pH 7.3) onto Maxisorp microtitre plates. Plates were blocked with 1% (w/v) BSA in standard assay buffer (20 mM HEPES, 130 mM NaCl, 0.05% (v/v) Tween-20, pH 7.3) for 90 minutes at 37° C. The standard assay buffer (SAB) was used for all subsequent incubations, dilutions and washes at room temperature unless otherwise stated. Biotinylated 4IS heparin (0.75 μg/well in 100 μl volume) was added in the presence of a range of concentrations of unlabelled 4IS heparin (0, 0.04, 0.4, 4, 40 400 and 4000 pmol/well) and incubated for four hours. Bound material was detected by adding 100 μl/well of a 1:5,000 dilution of ExtrAvidin alkaline phosphatase for 30 minutes. Plates were then developed with 100 μl/well of 1 mg/ml disodium p-nitrophenylphosphate in 50 mM Tris-HCl, 100 mM NaCl, pH 9.3, and developed for 20 minutes. The absorbance values were read at 405 nm and corrected against blank wells that contained no immobilised protein.

Results

Figure 15:
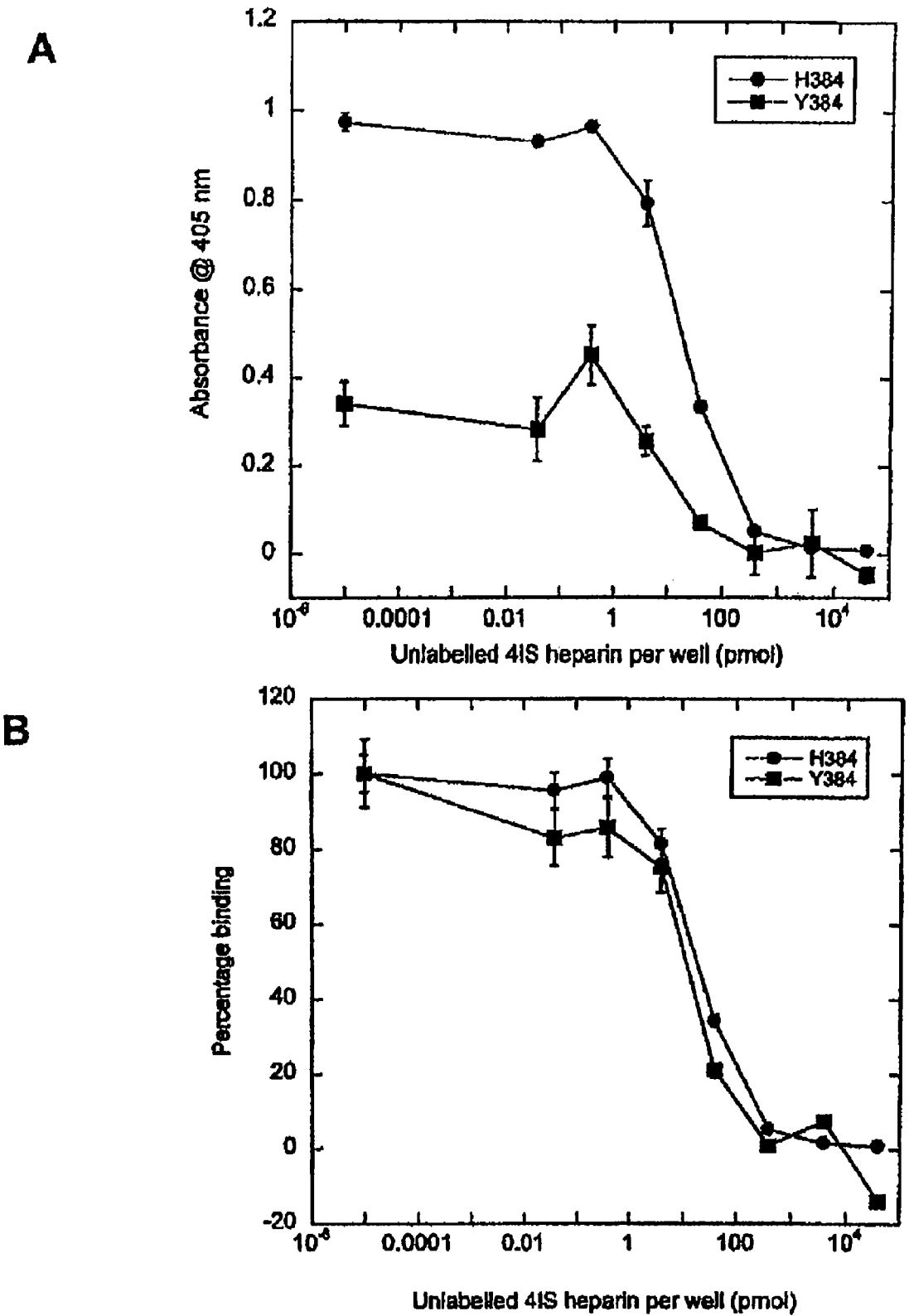

The binding of biotinylated 4IS heparin to immobilised FHCCP6-8(H384) and FHCCP6-8(Y384) proteins can be inhibited in a dose-dependent manner by addition of competing unlabelled 4IS heparin. As can be seen from FIG. 15, although the FHCCP6-8(H384) and FHCCP6-8(Y384) proteins exhibit different absolute levels of binding to biotinylated 4IS heparin (e.g. in the absence of competitor (FIG. 15A)), these interactions can be inhibited in the presence of competing unlabelled 4IS heparin, where the $IC_{50}$ values for the two proteins are essentially identical (FIG. 15B). Thus this assay system is suitable for the screening of molecules that can compete for heparin binding to Factor H and could be used to identify compounds that can differentially inhibit the H384 versus the Y384 variant.

TABLE 2

```
FHCCP68 (H384 ALLOTYPE)
MGTLKPCDYP DIKHGGLYHE NMRRPYFPVA VGKYYSYYCD
EHFETPSGSY WDHIHCTQDG WSPAVPCLRK CYFPYLENGY
NQNHGRKFVQ GKSIDVACHP GYALPKAQTT VTCMENGWSP
TPRCIRVKTC SKSSIDIENG FISESQYTYA LKEKAKYQCK
LGYVTADGET SGSITCGKDG WSAQPTCI*
(SEQ.ID.NO. 1)

FHCCP68 (H384 ALLELE)
atgggt acc ttgaaacctt gtgattatcc agacattaaa
catggaggtc tatatcatga gaatatgcgt agaccatact
ttccagtagc tgtaggaaaa tattactcct attactgtga
tgaacatttt gagactccgt caggaagtta ctgggatcac
attcattgca cacaagatgg atggtcgcca gcagtaccat
gcctcagaaa atgttatttt ccttatttgg aaaatggata
taatcaaaat catggaagaa agtttgtaca gggtaaatct
atagacgttg cctgccatcc tggctacgct cttccaaaag
cgcagaccac agttacatgt atggagaatg gctggtctcc
tactcccaga tgcatccgtg tcaaaacatg ttccaaatca
agtatagata ttgagaatgg gtttatttct gaatctcagt
atacatatgc cttaaaagaa aaagcgaaat atcaatgcaa
actaggatat gtaacagcag atggtgaaac atcaggatca
attacatgtg ggaaagatgg atggtcagct caacccacgt
gcatt taa
(SEQ ID NO: 2)
```

Histidine 384 of mature Factor H and the corresponding allelic nucleotide are shown in bold (and underlined).
The initiating methionine (underlined) is removed during expression and is not present in the recombinant protein.

Table 3

```
FHCCP68 (Y384 ALLOTYPE)
MGTLKPCDYP DIKHGGLYHE NMRRPYFPVA VGKYYSYYCD
EHFETPSGSY WDHIHCTQDG WSPAVPCLRK CYFPYLENGY
NQNYGRKFVQ GKSIDVACHP GYALPKAQTT VTCMENGWSP
TPRCIRVKTC SKSSIDIENG FISESQYTYA LKEKAKYQCK
LGYVTADGET SGSITCGKDG WSAQPTCI*
(SEQ ID NO: 3)

FHCCP68 (Y384 ALLELE)
atggt acc ttgaaacctt gtgattatcc agacattaaa
catggaggtc tatatcatga gaatatgcgt agaccatact
ttccagtagc tgtaggaaaa tattactcct attactgtga
tgaacatttt gagactccgt caggaagtta ctgggatcac
attcattgca cacaagatgg atggtcgcca gcagtaccat
gcctcagaaa atgttatttt ccttatttgg aaaatggata
taatcaaaat tatggaagaa agtttgtaca gggtaaatct
atagacgttg cctgccatcc tggctacgct cttccaaaag
cgcagaccac agttacatgt atggagaatg gctggtctcc
tactcccaga tgcatccgtg tcaaaacatg ttccaaatca
agtatagata ttgagaatgg gtttatttct gaatctcagt
atacatatgc cttaaaagaa aaagcgaaat atcaatgcaa
actaggatat gtaacagcag atggtgaaac atcaggatca
attacatgtg ggaaagatgg atggtcagct caacccacgt
gcatt taa
(SEQ ID NO: 4)
```

Tyrosine 384 of mature Factor H and the corresponding allelic nucleotide are shown in bold (and underlined).
The initiating methionine (underlined) is removed during expression and is not present in the recombinant protein.

The invention claimed is:

1. A method of identifying whether a test agent has the ability to preferentially inhibit binding of the H384 allotypic variant of Factor H to a target compared with the Y384 allotypic variant of Factor H said method comprising:
   (i) providing a target to which both said variants of Factor H will bind differentially;
   (ii) contacting said target, both in the presence and absence of the test agent, with each of said variants, or a recombinant protein presenting a target-binding fragment of each of said variants including amino acid residue 384 and capable of heparin binding via the heparin-binding residues of the Complement Control Protein module 7 (CCP7), under conditions whereby both variant proteins employed bind said target differentially in the absence of the test agent, and
   (iii) determining whether the test agent exhibits said ability;
   with the proviso that where the target provided is heparin it exhibits higher binding of the H384 variant protein employed than the Y384 variant protein employed in the absence of the test agent.

2. The method of claim 1, in which recombinant proteins are employed comprising target binding fragments of said allotypic variants of Factor H derived from the Complementary Control Protein (CCP) modules 6-8.

3. The method of claim 2, wherein said recombinant proteins are FHCCP6-8(H384) and FHCCP6-8(Y384) consisting of Complement Control Protein modules 6 to 8 of the allotypic variants of Factor H apart from an additional N-terminal methionine followed by a non-authentic glycine, FHCCP6-8(H384) having the sequence of SEQ ID NO: 1 and FHCCP6-8(Y384) having the sequence of SEQ ID NO: 3.

4. The method of claim 1, wherein said target is heparin which in the absence of test agent exhibits higher binding of the H384 allotypic variant protein employed than the Y384 allotypic variant protein employed in the absence of test agent.

5. The method of claim 4, wherein an unfractionated international standard heparin is employed as the target.

6. The method of claim 1, wherein said target is a sample of heparan sulphate which exhibits the desired differential binding of the protein variants employed such as bovine kidney heparan sulphate.

7. The method of claim 1, wherein said target is dermatan sulphate.

8. The method of claim 1, wherein said target is C-reactive protein or a portion thereof which binds CCPs 6-8 of Factor H.

9. The method of claim 1, wherein said target is fibromodulin, either glycosylated or preferably lacking some or all glycosylation, or a portion thereof which binds CCPs 6-8 of Factor H.

10. The method of claim 1, wherein said target is DNA which binds CCPs 6-8 of Factor H.

11. The method of claim 1, wherein said target is necrotic cells.

12. The method of claim 1, wherein said target is immobilized on a plate and the variant proteins are labelled or the variant proteins are immobilized on a plate and said target is labelled.

13. The method of claim 12, wherein said target selected from heparin, heparan sulphate or dematan sulphate is immobilized on an allylamine-coated plate.

14. The method of claim 12, wherein said target or the variant proteins are biotinylated.

* * * * *